US012333783B2

(12) United States Patent
Mauldin, Jr. et al.

(10) Patent No.: US 12,333,783 B2
(45) Date of Patent: Jun. 17, 2025

(54) SYSTEM AND METHOD FOR ULTRASOUND SPINE SHADOW FEATURE DETECTION AND IMAGING THEREOF

(71) Applicant: Rivanna Medical LLC, Charlottesville, VA (US)

(72) Inventors: Frank William Mauldin, Jr., Charlottesville, VA (US); Adam Dixon, Charlottesville, VA (US)

(73) Assignee: Rivanna Medical, Inc., Charlottesville, VA (US)

(*) Notice: Subject to any disclaimer, the term of this patent is extended or adjusted under 35 U.S.C. 154(b) by 664 days.

(21) Appl. No.: 16/316,432

(22) PCT Filed: Aug. 18, 2017

(86) PCT No.: PCT/US2017/047472
§ 371 (c)(1),
(2) Date: Jan. 9, 2019

(87) PCT Pub. No.: WO2018/035392
PCT Pub. Date: Feb. 22, 2018

(65) Prior Publication Data
US 2019/0192114 A1 Jun. 27, 2019

Related U.S. Application Data

(60) Provisional application No. 62/376,770, filed on Aug. 18, 2016.

(51) Int. Cl.
G06V 10/764 (2022.01)
A61B 8/00 (2006.01)
(Continued)

(52) U.S. Cl.
CPC .......... *G06V 10/764* (2022.01); *A61B 8/0841* (2013.01); *A61B 8/085* (2013.01);
(Continued)

(58) Field of Classification Search
CPC .................................................. G06T 7/10–13
See application file for complete search history.

(56) References Cited

U.S. PATENT DOCUMENTS

| 4,476,873 A | 10/1984 | Sorenson et al. |
| 2003/0179915 A1* | 9/2003 | Goto .................... G06T 7/0012 |
| | | 382/128 |

(Continued)

FOREIGN PATENT DOCUMENTS

| CN | 104637044 A | * | 5/2015 | ............. A61B 8/085 |
| JP | 2010207492 A | * | 9/2010 | |

(Continued)

OTHER PUBLICATIONS

Chin et al., "Ultrasonography of the Adult Thoracic and Lumbar Spine for Central Neuraxial blockade", Anesthesiology, vol. 114, No. 6. Jun. 2011, pp. 1459-1485 (Year: 2011).*

(Continued)

Primary Examiner — Shahdeep Mohammed
Assistant Examiner — Farouk A Bruce
(74) Attorney, Agent, or Firm — Wood Rogers Vandeventer Black PLC; Nathan A. Evans

(57) ABSTRACT

Systems and methods for anatomical identification using ultrasonic imaging and acoustic shadow detection methods are provided. At least some embodiments of the disclosure comprise the following steps: acquiring ultrasound image; detecting shadow region; extracting shadow profile; filtering shadow profile with matched filter; identifying anatomical landmarks within shadow; extracting features of anatomical landmarks; classifying anatomy, and determining with a high degree of confidence that the target anatomy is depicted in the image. A determination is made as to the degree of confidence that the target anatomy is depicted in the image. Conditionally, graphics indicating presence and position of (Continued)

target anatomy is displayed including disposition, location and orientation thereof.

16 Claims, 15 Drawing Sheets

(51) Int. Cl.
 *A61B 8/08*    (2006.01)
 *G06F 18/24*   (2023.01)
 *G06T 7/12*    (2017.01)
 *G06T 7/13*    (2017.01)
 *G06V 20/64*   (2022.01)
 *G16H 30/40*   (2018.01)

(52) U.S. Cl.
 CPC .......... *A61B 8/0875* (2013.01); *A61B 8/5207* (2013.01); *A61B 8/5246* (2013.01); *G06F 18/24* (2023.01); *G06V 20/653* (2022.01); *A61B 8/4427* (2013.01); *G06T 7/12* (2017.01); *G06T 7/13* (2017.01); *G06V 2201/03* (2022.01); *G16H 30/40* (2018.01)

(56) References Cited

U.S. PATENT DOCUMENTS

| | | | |
|---|---|---|---|
| 2003/0216648 A1* | 11/2003 | Lizzi | A61B 8/0858 601/2 |
| 2005/0113695 A1* | 5/2005 | Miller | G01S 7/52046 600/443 |
| 2006/0206032 A1* | 9/2006 | Miele | A61B 8/0858 600/481 |
| 2012/0243757 A1* | 9/2012 | Funka-Lea | G06T 7/0002 382/131 |
| 2014/0005542 A1 | 1/2014 | Bizzell et al. | |
| 2015/0223777 A1 | 8/2015 | Rasoulian et al. | |
| 2016/0012582 A1 | 1/2016 | Mauldin, Jr. et al. | |
| 2016/0249879 A1* | 9/2016 | Mauldin, Jr. | A61B 8/5223 600/437 |

FOREIGN PATENT DOCUMENTS

| | | |
|---|---|---|
| WO | 20140134188 A1 | 9/2014 |
| WO | WO2014134188 A1 | 9/2014 |

OTHER PUBLICATIONS

Ashab, H.A., et al., "An Augmented Reality System for Epidural Anesthesia (AREA): Prepuncture Identification of Vertebrae", IEEE Transactions on Biomedical Engineering, vol. 60, No. 9, Sep. 2013. pp. 2636-2644. (Year: 2013).*

Berton, F., et al., "Segmentation of the Spinous Process and its Acoustic Shadow in Vertebral Ultrasound images", Computers in Biology and Medicine 72 (2016) 201-211. (Year: 2016).*

Berton Florian et al: "Automatic Segmentation o f Vertebrae i n Ultrasound Images", Jul. 4, 2015 (Jul. 4, 2015), International Conference On Financial Cryptography and Data Security; [Lecture Notes in Computer Science; Lect.Notes Computer], Springer, Berlin, Heidelberg, pp. 344-351, XP047314473, ISBN: 978-3-642-17318-9.

Berton Florian et al: "Segmentation of the spinous process and its acoustic shadow in vertebral ultrasound images", Computers in Biology and Medicine, New York, NY, US, vol. 72, Mar. 26, 2016 (Mar. 26, 2016), pp. 201-211, XP029511357, ISSN: 0010-4825, DOI: 10.1016/J.COMPBIOMED.2016.03.018.

Extended European Search Report in European Application No. 17842161.6, dated Mar. 9, 2020, 6 pages.

W.J. Vander Beek, "Use of the Portable Ultrasound to Determine Favorable Level and Angle for Epidural Puncture.", Providence St. Peter Hospital, Olympia, WA, Anesthesia Support Department, 2006, pp. 1-12.

ISA, "International Search Report", PCT/US2017/047472, Nov. 6, 2017.

* cited by examiner

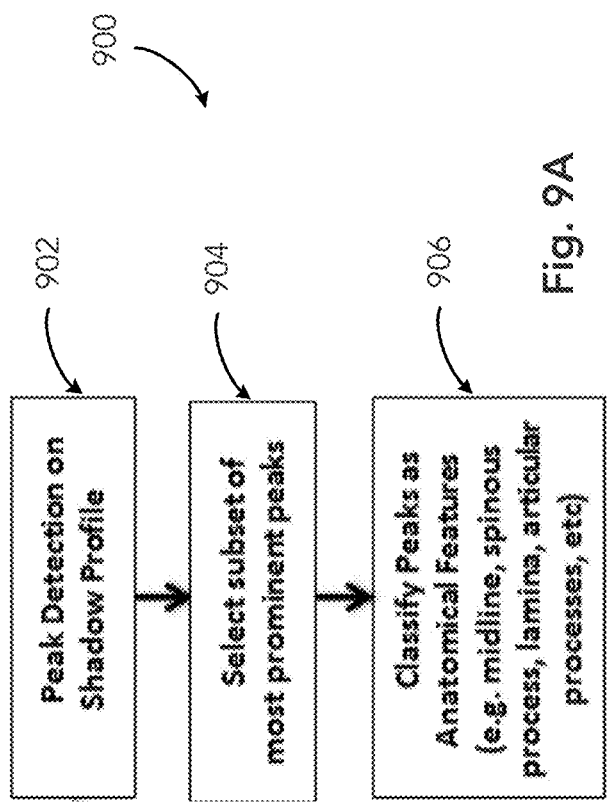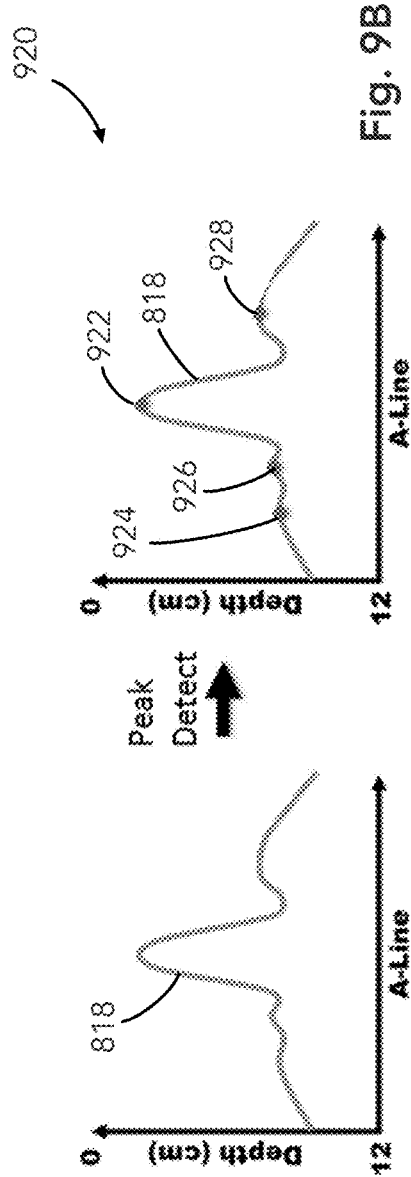

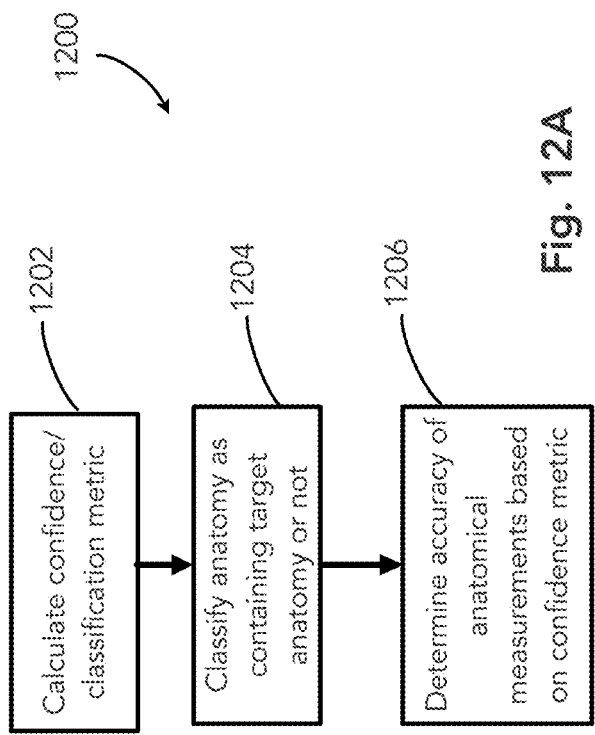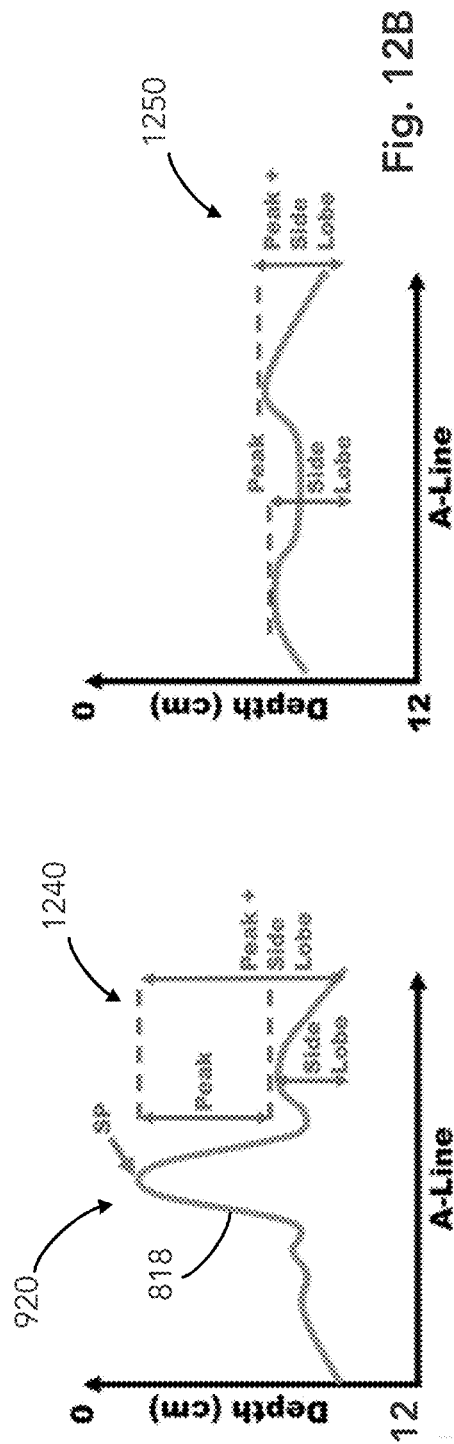

SYSTEM AND METHOD FOR ULTRASOUND SPINE SHADOW FEATURE DETECTION AND IMAGING THEREOF

RELATED APPLICATIONS

This application is a U.S. National Phase application under 35 U.S.C. § 371 of International Application No. PCT/US2017/047472, entitled "System and Method for Ultrasound Spine Shadow Feature Detection and Imaging Thereof", filed on Aug. 18, 2017, and claims the benefit of and priority to U.S. Provisional Application No. 62/376,770, filed on Aug. 18, 2016, entitled "SYSTEM AND METHOD FOR ULTRASOUND SPINE SHADOW FEATURE DETECTION AND IMAGING THEREOF", both of which are incorporated by reference herein in its their entirety.

STATEMENT OF FEDERALLY SPONSORED RESEARCH

This invention was made with government support under R44EB015232 awarded by the National Institute of Biomedical Imaging and Bioengineering of the National Institutes of Health and under 1329651 awarded by the National Science Foundation. The U.S. Government has certain rights in the invention.

TECHNICAL FIELD

The present disclosure is directed to ultrasound imaging and systems and methods for ultrasonic image acquisition and generation. Aspects of the disclosure relate to generating ultrasound images of bone and/or visualizing ultrasound images of bone in a subject being imaged. Specifically, the present invention pertains to spinous shadow feature detection and displaying ultrasound imaging a real-time feedback thereof through a graphical user interface for the purpose of probe insertion.

BACKGROUND

Medical ultrasound may be used as an alternative to X-ray for bone imaging. However, conventional ultrasound systems are limited in their application. For example, in many conventional ultrasound systems, artifacts may be generated from off-axis reflections, which make the produced image less useful to the user. In addition, many conventional systems produce difficult-to-interpret two-dimensional (2D) images. Although certain transducer geometries may be used to reduce artifacts and three-dimensional (3D) ultrasound images of bone may be obtained, such images nonetheless generally suffer from low sensitivity, as the ultrasound signal strength is highly dependent on the angle of the bone surface with respect to the acoustic beam axis.

Various medical procedures comprise penetrating the skin with a probe, such as a needle or a catheter. For example, spinal anesthesia or a spinal diagnostic procedure can include percutaneous delivery of anesthetic to an epidural location or sampling of spinal fluid. Such spinal anesthesia or spinal diagnostic procedures generally include penetrating the ligamentum flavum, a ligament between the spinous processes lateral to the dura. Generally, a desired final needle position during epidural placement is posterior of the dura, while in a spinal tap, the dura is penetrated in order to obtain fluid from the spinal cavity.

Spinal taps have several important clinical applications including sampling cerebral spinal fluid (CSF), administering chemotherapy or other drugs directly into the spinal cavity, or relieving pressure in the spinal cavity for cardiac procedures. Sampling of CSF can also be necessary to quickly diagnose various diseases such as meningitis. Other procedures can similarly include penetrating the skin with a probe, such as paravertebral somatic nerve blockade (PVB).

Neuraxial anesthesia blocks (e.g., epidural anesthesia or spinal anesthesia blocks) and related spinal anesthesia procedures are presently performed in approximately 18 million procedures per year in U.S. hospitals. Numerous clinical indications for such procedures include anesthesia during pregnancy, chronic pain, or hip or knee replacement surgery.

Given the importance of probe placement due its sensitive location, imaging can be used to ameliorate probe guidance. In one approach, fluoroscopy can be used to guide spinal needle placement with high success. However, the risk of ionizing radiation, in addition to high cost and lack of portability of fluoroscopy equipment, make fluoroscopy an unattractive option for a high-volume procedure.

Other x-ray based medical imaging techniques can also be effective but suffer from the similar risks and disadvantages. For example, computed tomography (CT) and 2-dimensional x-ray projection are frequently used as imaging modalities for bone imaging. Unfortunately, ionizing radiation exposure to patients and caregivers from such medical imaging has increased dramatically in past decades (estimated at 600% increase since the 1980's). The cumulative effect of such radiation dosages has been linked to increased risk of cancer.

During a medical procedure, a probe insertion can sometimes be accomplished without requiring medical imaging (i.e., using an unguided technique). A blind approach comprises needle insertion after locating spinal bone landmarks using manual palpation. However, such unguided techniques can sometimes fail. Unguided spinal anesthesia or spinal diagnostic procedure failures typically occur in the elderly or morbidly obese. Reasons for failure in unguided procedures include incorrect needle insertion location or use of an incorrect needle angle during penetration.

Consequently, in a spinal anesthesia or a spinal diagnostic procedure, failure can prevent access to the spinal cavity or preclude placement of a needle or catheter lateral the dura for administration of an epidural. Failure rates for blind approaches have been historically cited as between 40%-80% in patient populations exhibiting landmarks that are absent, indistinct, or distorted.

A significant and growing population segment exhibiting these characteristics is the obese that currently make up 33.9% of the total U.S. population but represent a disproportionately high blind failure rate. That is, failure of unguided procedures can occur at rates as high of 74% of cases involving obese patients. Such failures can increase healthcare costs, such as those arising from complications requiring additional treatment.

In the morbidly obese, such failure can occur because anatomical landmarks (e.g., spine) cannot be reliably palpated due to thick layers of fatty tissue between the landmarks and the skin. Failures generally result in multiple needle sticks, which are correlated with poor health outcomes such as an increased risk of spinal headache or hematoma. In addition, other serious complications can occur from failed neuraxial anesthesia including back pain (30%), or vascular puncture (3.8%), as well as more severe complications including pleural puncture (1.1%), pneumothorax (0.5%), or paralysis (rare). Such complications can include spinal headaches, back pain, paraparesis, spinal hematoma, nerve palsy, spinal tumor formation, or one or more other complications.

Generally, when the unguided approach fails, clinical procedure includes using fluoroscopy or other guided procedures to assist in probe placement. Medical ultrasound may be used as an alternative to x-ray for bone imaging.

SUMMARY

Even though they don't pose the risk of ionizing radiation, conventional ultrasound systems are limited in their application. Ultrasound systems currently in use are generally large, complicated, and expensive and require specialized training to operate.

Additionally, failure rates can still remain high, and the success of ultrasonic techniques has generally been highly dependent on user familiarity with ultrasonography.

The present inventors have recognized, among other things, a need for a more portable solution for guidance to and/or location of anatomical features which can be operated without extensive training in ultrasonography.

Such a hand-held apparatus can be simpler to operate than generally available ultrasound imaging equipment. For example, information provided by a hand-held apparatus can be less resource consuming and simpler to interpret—in contrast to generally available B-mode ultrasonic imaging equipment. The proposed apparatus can enable more accurate puncture or probe insertion procedures by providing information to the user about a depth or location of bone with respect to the probe.

The present inventors have also recognized that a portable apparatus can be less expensive than generally available B-mode imaging equipment. Also, incorporation of display into a hand-held device can be manufactured to provide an intuitive or easy-to-understand indication of a bone location or depth, as compared to a B-mode sonogram that can be difficult to interpret. Use of the hand-held apparatus can also reduce medical costs because the hand-held apparatus can be used for guided probe insertion or anatomical location thereby reducing likelihood of failure or complication during a probe insertion.

The prior art generally lacks a usable guidance system for probe insertion using non-ionizing ultrasonic imaging.

Moreover, while the error of reconstructed bone surfaces may be very low, the low specificity and sensitivity of the reconstruction may still yield an image that is challenging to interpret. Additionally, the production of freehand images in 3D remains challenging due to, for example, cumulative motion estimation bias distortions. For at least these reasons, ultrasound images generated by conventional ultrasound imaging techniques remain difficult to interpret.

The inventors have also recognized that an ultrasound image comprising bone may be easier to interpret if presented (e.g., to a user) with reference to an anatomical model of the bone being imaged.

The present disclosure contemplates, among other things, the novel fabrication of a portable device with ultrasound imaging that utilizes bone shadow detection methods depicted on a graphical user interface (GUI) for giving user feedback of probe insertion, depth, disposition, location and orientation, as well as practical methods for the application thereof and remedying these and/or other associated problems.

According to one aspect of the invention, automated spine landmark identification is generated, based at least in part on, information contained in an acoustic shadow of the ultrasound images. According to some aspects, shadow is detected automatically from the acoustic data via a shadow filter.

According to one or more aspects of the invention, shadow information is sufficient for classifying anatomy within the ultrasound image as one of the following: epidural space, spinous process, etc. According to other aspects of the invention, other identifiable landmarks include: sacrum, spine midline, etc.

According to one aspect of the invention, information provided to the user comprises the following: location of spinous process(es), location of epidural spaces(s), location of spine midline, location of sacrum, depth to spinous process tip, depth to epidural space and/or angular rotation of spine.

According to one or more aspects, a method, comprises: obtaining ultrasound data generated based, at least in part, on one or more ultrasound signals from an imaged region of a subject; determining a shadow profile based at least in part on the ultrasound data; identifying, based at least in part on the shadow profile, an anatomical structure present in the imaged region; generating, based at least in part on the shadow profile, a classification of the anatomical structure; and displaying, on a display of a handheld ultrasound imager, a composite image based at least in part on the ultrasound data and based at least in part on the classification of the anatomical structure.

According to one or more aspects, at least one non-transitory computer readable storage medium stores processor-executable instructions that, when executed by at least one processor, result in the method.

According to one or more aspects, a system comprises at least one computer hardware processor configured to perform a method comprising: using at least one computer hardware processor to perform: obtaining ultrasound data generated based, at least in part, on one or more ultrasound signals from an imaged region of a subject; determining a shadow profile based at least in part on the ultrasound data; identifying, based at least in part on the shadow profile, an anatomical structure present in the imaged region; and generating, based at least in part on the shadow profile, a classification of the anatomical structure; and a handheld ultrasound imager to display a composite image based at least in part on the ultrasound data and based at least in part on the classification of the anatomical structure.

In at least some embodiments, the ability to classify anatomical structures and generate a composite image for display by a handheld imager facilitates a more portable solution for guidance to and/or location of anatomical features which can be operated without extensive training in ultrasonography. In at least some embodiments, such a handheld imager may be simpler to operate than generally available ultrasound imaging equipment. For example, in at least some embodiments, it enables more accurate puncture or probe insertion procedures by providing information to a person viewing the display about a depth and/or location of bone (and/or other structure(s)) with respect to the probe. In at least some embodiments, a handheld imager that displays the composite image is less expensive than generally available B-mode imaging equipment. Also, in at least some embodiments, the composite image disclosed herein provides an intuitive or easy-to-understand indication of a bone location or depth (or other structures and/or details in regard thereto) on a handheld imager, as compared to merely a B-mode sonogram on the handheld imager that can be difficult to interpret. In at least some embodiments, it can also reduce medical costs because the hand-held apparatus can be used for guided probe insertion or anatomical location thereby reducing likelihood of failure or complication during a probe insertion or other medical procedure.

In at least some embodiments, said determining, by a processor, a shadow profile based at least in part on the ultrasound data comprises: determining a shadow image region based at least in part on the ultrasound data; and determining, by a processor and based at least in part on the shadow image region, a shadow profile.

In at least some embodiments, said identifying, based at least in part on the shadow profile, an anatomical structure present in the imaged region comprises: receiving information indicative of a target anatomy; determining an anticipated shadow based at least in part on the information indicative of the target anatomy; determining a measure of similarity between the shadow profile and the anticipated shadow; and identifying, based at least in part on the measure of similarity between the shadow profile and the anticipated shadow, an anatomical structure present in the imaged region.

In at least some embodiments, said identifying, based at least in part on the shadow profile, an anatomical structure present in the imaged region comprises: receiving information indicative of a target anatomy; determining an anticipated shadow based at least in part on the information indicative of the target anatomy; and identifying, based at least in part on the shadow profile and the anticipated shadow, an anatomical structure present in the imaged region.

In at least some embodiments, said identifying, based at least in part on the shadow profile, an anatomical structure present in the imaged region comprises: identifying a feature in the shadow profile; and classifying the feature in the shadow profile as a specific anatomical feature.

In at least some embodiments, said identified feature in the shadow profile is a peak in the shadow profile; and wherein said classifying the feature as a specific anatomical feature comprises: classifying the peak in the shadow profile as a specific anatomical feature.

In at least some embodiments, the specific anatomical feature is a midline.

In at least some embodiments, the method further comprises: identifying a second feature in the shadow profile; and comparing the feature in the shadow profile and the second feature in the shadow profile.

In at least some embodiments, the comparing the feature in the shadow profile and the second feature in the shadow profile comprises: determining a metric for the feature in the shadow profile; determining a metric for the second feature in the shadow profile; and comparing the metric for the feature in the shadow profile and the metric for the second feature in the shadow profile.

In at least some embodiments, the comparing the metric for the feature in the shadow profile and the metric for the second feature in the shadow profile comprises: determining a difference of the metric for the feature in the shadow profile and the metric for the second feature in the shadow profile.

In at least some embodiments, the comparing the metric for the feature in the shadow profile and the metric for the second feature in the shadow profile comprises: determining a difference of the metric for the feature in the shadow profile and the metric for the second feature in the shadow profile.

In at least some embodiments, the comparing the metric for the feature in the shadow profile and the metric for the second feature in the shadow profile comprises: determining a ratio of the metric for the feature in the shadow profile and the metric for the second feature in the shadow profile.

In at least some embodiments, the identifying, based at least in part on the shadow profile, an anatomical structure present in the imaged region comprises: filtering the shadow profile; and identifying, based at least in part on the filtered shadow profile, an anatomical structure present in the imaged region.

In at least some embodiments, the determining, a shadow profile based at least in part on the ultrasound data comprises: determining, shadow intensity data based at least in part on the ultrasound data; and determining a shadow profile based at least in part on non-linear processing of the shadow intensity data.

Some embodiments employ an imaging method, comprising using at least one computer hardware processor to perform: obtaining ultrasound data generated based, at least in part, on one or more ultrasound signals from an imaged region of a subject, the ultrasound data comprising fundamental frequency ultrasound data and harmonic frequency ultrasound data, calculating shadow intensity data based at least in part on the harmonic frequency ultrasound data, generating, based at least in part on the fundamental frequency ultrasound data, an indication of bone presence in the imaged region, generating, based at least in part on the shadow intensity data, an indication of tissue presence in the imaged region, and generating an ultrasound image of the subject at least in part by combining the indication of bone presence and the indication of tissue presence.

Some embodiments employ an ultrasound imaging system comprising at least one computer hardware processor configured to perform obtaining ultrasound data generated based, at least in part, on one or more ultrasound signals from an imaged region of a subject, the ultrasound data comprising fundamental frequency ultrasound data and harmonic frequency ultrasound data, calculating shadow intensity data based at least in part on the harmonic frequency ultrasound data, generating, based at least in part on the fundamental frequency ultrasound data, an indication of bone presence in the imaged region, generating, based at least in part on the shadow intensity data, an indication of tissue presence in the imaged region, and generating an ultrasound image of the subject at least in part by combining the indication of bone presence and the indication of tissue presence.

Some embodiments employ at least one non-transitory computer readable storage medium that storing processor-executable instructions that, when executed by at least one processor, cause the at least one processor to perform an ultrasound imaging method. The method comprises obtaining ultrasound data generated based, at least in part, on one or more ultrasound signals from an imaged region of a subject, the ultrasound data comprising fundamental frequency ultrasound data and harmonic frequency ultrasound data; calculating shadow intensity data based at least in part on the harmonic frequency ultrasound data, generating, based at least in part on the fundamental frequency ultrasound data, an indication of bone presence in the imaged region, generating, based at least in part on the shadow intensity data, an indication of tissue presence in the imaged region, and generating an ultrasound image of the subject at least in part by combining the indication of bone presence and the indication of tissue presence.

This Summary is intended to provide an overview of at least some of the subject matter of the present patent application. It is not intended to provide an exclusive or exhaustive explanation of the invention or embodiments thereof.

Thus, while certain aspects and embodiments have been presented and/or outlined in this Summary, it should be understood that the present aspects and embodiments are not limited to the aspects and embodiments in this Summary. Indeed, other aspects and embodiments, which may be similar to and/or different from, the aspects and embodiments presented in this Summary, will be apparent from the description, illustrations and/or claims, which follow.

Further limitations and disadvantages of conventional and traditional approaches will become apparent to one of skill in the art, through comparison of such systems with some aspects of the present invention as set forth in the remainder of the present application with reference to the drawings.

However, while various features and/or advantages are described in this Summary and/or will become apparent in view of the following detailed description and accompanying drawings, it should be understood that such features and/or advantages are not required in all aspects and embodiments.

Any aspects and/or embodiments that are described in this Summary and do not appear in the claims that follow are preserved for later presentation in this application or in one or more continuation patent applications. Any aspects and/or embodiments that are not described in this Summary and do not appear in the claims that follow are also preserved for later presentation or in one or more continuation patent applications.

BRIEF DESCRIPTION OF THE DRAWINGS

For a fuller understanding of the nature and advantages of the present invention, reference is made to the following detailed description of preferred embodiments and in connection with the accompanying drawings, in which:

FIG. 9A is a flowchart of a method, in accordance with some embodiments;

FIG. 9B depicts a convolved exemplary filtered shadow profile and the application of peak detection thereto for the purpose of sonoanatomy, in accordance with some embodiments of the disclosure provided herein;

FIG. 12A is a flowchart of a method, in accordance with some embodiments;

FIG. 12B depicts a convolved exemplary filtered shadow profile, the application of peak detection thereto and extraction of associated metrics for the purpose of sonoanatomy, in accordance with some embodiments of the disclosure provided herein;

DETAILED DESCRIPTION

Figure 1:
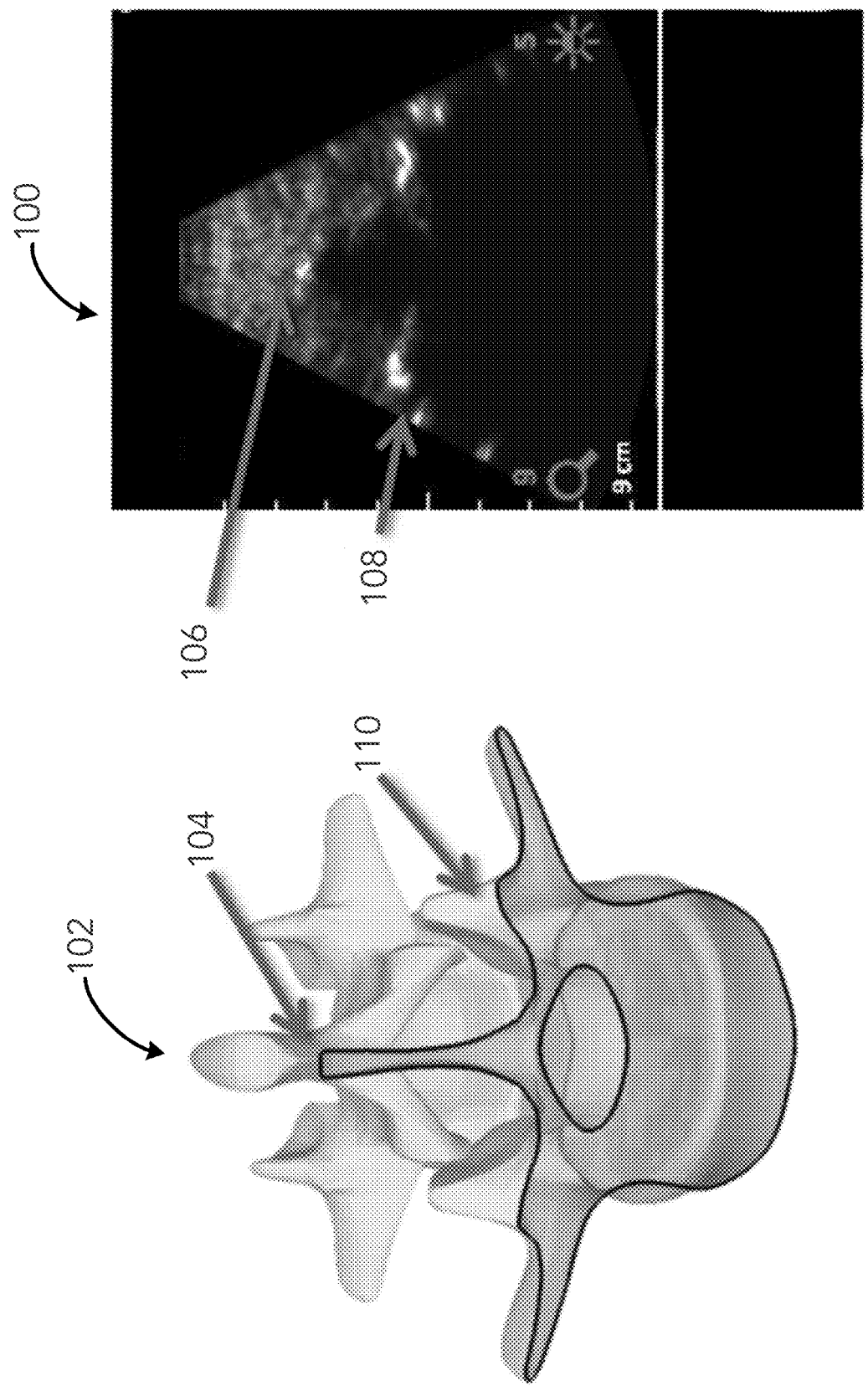
FIG. 1 illustrates a visualization of a 2D ultrasound image of an imaged area together with a 3D model of the sonoanatomy of the spinous process, in accordance with some embodiments of the disclosure provided herein.

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure are set forth herein in view of the drawings where applicable. However, while various objects, features and/or advantages are described herein and/or will become apparent in view of the following detailed description and accompanying drawings, it should be understood that such, objects, features and/or advantages are not required in all aspects and embodiments. Reference is made to U.S. Provisional Application No. 62/120,999, by the present Applicant, filed on Feb. 26, 2015, entitled "System and Method for Ultrasound Imaging of Regions Containing Bone Structure," which is incorporated herein by reference in its entirety.

At least some embodiments, of the present invention are directed to probe guidance and insertion based on sonographic imaging of anatomical features. The inventors have recognized that unguided needle insertion for medical procedures exhibit substantial failure rates in an increasing demographic of the population. Anatomical features cannot be accurately palpated in all patients. Imaging an area of a subject which circumscribes the procedural location and identifying regions of bone and tissue for the generation of ultrasound images greatly augments the success probe insertion success rates.

Ultrasound is sound waves with frequencies which are higher than those audible to humans (e.g., above 20,000 Hz). Ultrasonic images also known as sonograms are made by sending pulses of ultrasound into tissue using a probe. The sound echoes off the tissue; with different tissues reflecting varying degrees of sound. These echoes are recorded and displayed as an image to the operator, as shown on the right of FIG. 1 (as will be further discussed below).

Medical ultrasound (also known as diagnostic sonography or ultrasonography) is a diagnostic imaging technique based on the application of ultrasound. It is used to see internal body structures such as tendons, muscles, joints, vessels and internal organs.

The inventors have also recognized that an ultrasound image comprising bone may be easier to interpret if presented (e.g., to a user) with reference to an anatomical model of the bone being imaged. Accordingly, some embodiments relate to visualizing ultrasound data by generating a visualization of a two-dimensional (2D) ultrasound image that includes a corresponding portion of a three-dimensional (3D) bone model. The corresponding portion of the 3D model (e.g., a 2D cross-section) may be identified at least in part by using a registration technique to register the 2D ultrasound image to the 3D model. The registration results may be used to identify the location(s) of one or more anatomical landmarks in the 2D ultrasound image and the generated visualization of the image may indicate one or more of the identified locations.

Aspects of the technology described herein are explained in the context of spinal anesthesia guidance, but it should be appreciated that the technology described herein is useful for and may be applied in other settings. For example, the technology described herein may be used for other clinical applications where ultrasound is used to image bone such as, but not limited to, guiding of orthopedic joint injections, performing lumbar punctures, or performing diagnosis of bone fractures.

In addition, while the present disclosure focuses its description in the context of ultrasonic transducers arranged in the transverse direction, ultrasonic transducer oriented in the longitudinal direction (and resulting longitudinal imaging) is not beyond the scope of the present invention. In fact, two dimensional planes of ultrasonic transducers and/or some combination of transverse and longitudinal imaging are also in the possession of the inventors of the present disclosure.

The inventors also recognize the efficacy of displaying the model relative to the probe guided device in a simple, easy to understand manner—particularly, with comprehensive, globally-recognizable symbolism. In some embodiments, a method for performing ultrasound imaging with a graphical user interface (GUI) is employed. The method may comprise building a 3D model based on patient anatomical features in conjunction with known models and/or predetermined patient models such as those derived from a priori MRIs or CAT scans, at least in part.

In some embodiments, the method comprises registering at least one 2D ultrasound image to a 3D model of a region comprising bone; and producing a 2D and/or 3D visualization of the region comprising bone wherein the visualization is derived, at least in part, from the registration of the at least one 2D ultrasound image to the 3D model of the spine. Registration can be performed by ultrasonically surveying a substantial portion of a patient's spine; performing an acoustic shadowing method to the survey; accessing existing libraries and analyzing its contents with respect to pattern matching to patient's sonogram; and/or loading 3D model from a previously performed scan (e.g., MRI, etc.) of the patient.

The aspects and embodiments described above, as well as additional aspects and embodiments, are described further below. These aspects and/or embodiments may be used individually, all together, or in any combination of two or more, as the technology described herein is not limited in this respect.

FIG. 1 illustrates a visualization of a 2D ultrasound image 100 (sometimes referred to as ultrasonogram 100 or ultrsonography 100) of an imaged area together with a 3D model 102 of a portion of a human spine (including the sonoanatomy of the spinous process), in accordance with some embodiments of the disclosure provided herein.

Spinous process is a bony projection off the posterior (back) of each vertebra of the human spin. The spinous process protrudes where the laminae of the vertebral arch join and provides the point of attachment for muscles (not shown) and ligaments (not shown) of the spine. Spinous processes are the ridges that can be felt through the skin along the back of the spine.

Thus, FIG. 1 juxtaposes the spinal anatomy with the corresponding ultrasonography. In one or more embodiments of the present invention, B-mode ultrasonography is utilized to identify one or more spinal regions. B-mode imaging displays the acoustic impedance of a two-dimensional cross-section of tissue. In the present embodiment, the device is oriented transversely to the spine and orthogonally to the plane of the patient's back. Therefore, ultrasonogram 100 illustrates the varying densities (acoustic impedance) of the patient's tissue and bone as a function of the acoustic wave penetrating from the surface of the back.

In practice, a device imaging in the transverse orientation relative to the spine is disposed close to a patient's back. It may be desirable to traverse the imaging device in the longitudinal direction relative to the spine in order to find and identify another spinal location. However, with respect to FIG. 1, the imaging device displays its current location proximal to the spinous process.

Those skilled in the art may recognize the spinous process as the center boney protrusion depicted at 104 on the 3D model 102. The corresponding anatomy is depicted at 106 at the top of the ultrasonogram 100, which as stated above may be a B-mode ultrasonogram. Referring again to FIG. 1, the projection of the spinous process in the ultrasonogram 100 is the dark shadow that is disposed at the top of the ultrasonogram 100 and is substantially triangular in shape. Also in shadow in the ultrasonography 100 is a depiction 108 of an articular process (which is disposed under the shadowed triangle 106 representing the spinous process) which corresponds to the articular process depicted at 110 on the 3D model 102.

The articular process is either of two processes, i.e., superior processes and inferior processes, on each side of a vertebra that articulate with adjoining vertebrae. The superior processes project upward from a lower vertebra, and their articular surfaces are directed more or less backward (oblique coronal plane). The inferior processes project downward from a higher vertebra, and their articular surfaces are directed more or less forward and outward.

Figure 2:
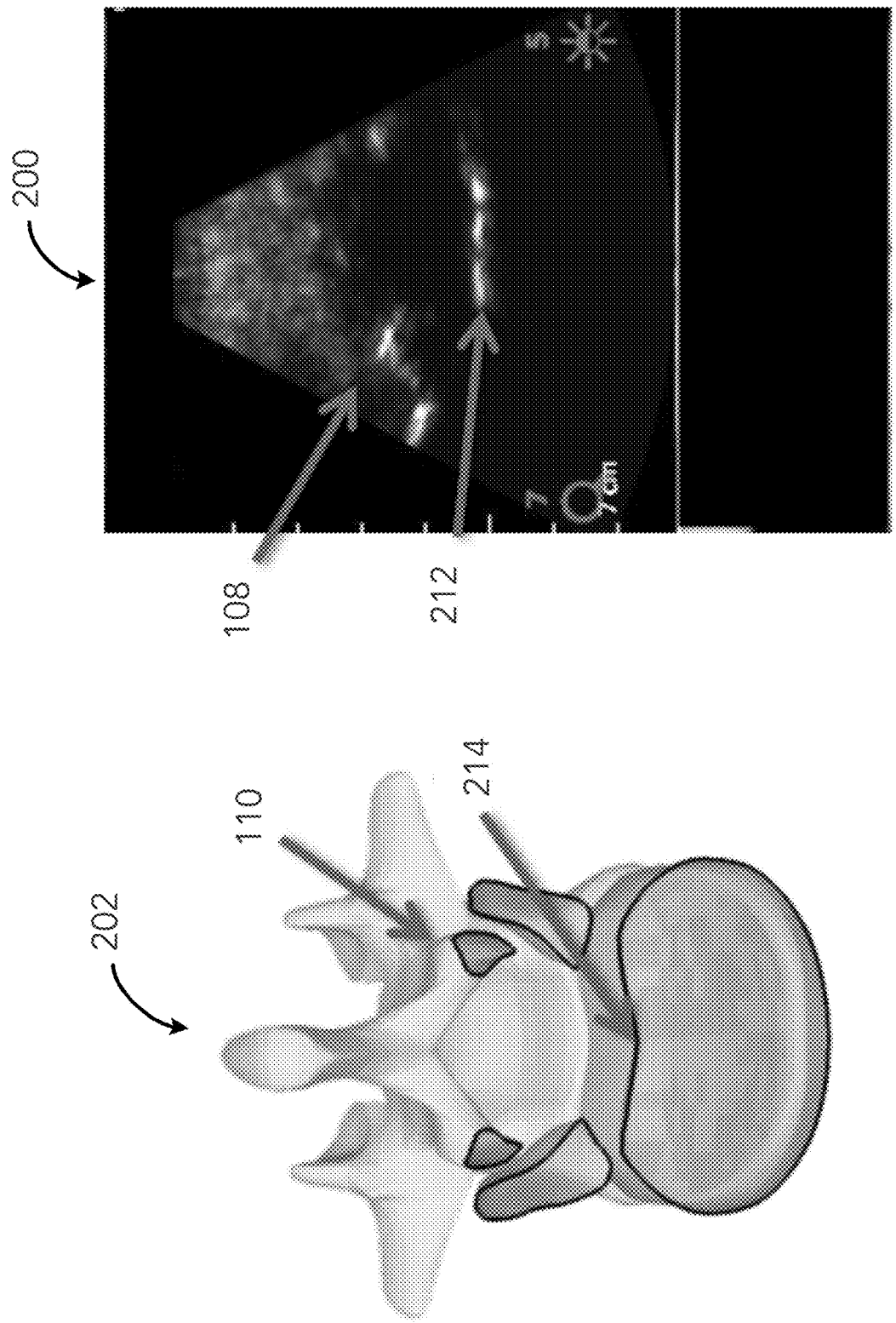
FIG. 2 illustrates a visualization of a 2D ultrasound image of an imaged area together with a 3D model of the sonoanatomy of the interlaminar space, in accordance with some embodiments of the disclosure provided herein.

FIG. 2 illustrates a visualization of a 2D ultrasound image 200 (sometimes referred to as ultrasonogram 200 or ultrsonography 200) of an imaged area together with a 3D model 202 of a portion of a human spine (including the sonoanatomy of the interlaminar space), in accordance with some embodiments of the disclosure provided herein. As discussed, it may be desirable to traverse the spine in the longitudinal direction. The ultrasonogram 200 of FIG. 2. Illustrates the cross-sectional area between two spinous processes. That is, if a practitioner moved the device below the location shown in FIG. 1, he/she would discover an area predominated by the vertebral body as seen in FIG. 2 at 212 of the ultrsonography 200 corresponding to 214 of the 3D model.

Also called the centrum, the vertebral body is the thick oval segment of bone forming the front of the vertebra. The cavity of the vertebral body consists of cancellous bone tissue and is encircled by a protective layer of compact bone. Bony structures called pedicles protrude from each side of the vertebral body and join with the laminae to form the vertebral arch. The upper and lower surfaces of the vertebral body are flat and rough to provide attachment for the vertebral discs that lie between each vertebra.

Upon analysis of the ultrasonogram 200 depicted in FIG. 2, a practitioner recognizes the interlaminar space above the vertebral body portrayed by a darkened shadow in the shape of a "U" or "V".

Also recognizable is the superior articular process (i.e., of the articular process depicted at 108, 110), which is disposed on either side of the interlaminar space. The tissue-bone interface appears relatively brighter while the region below said interface appears relatively darker.

Figure 3:
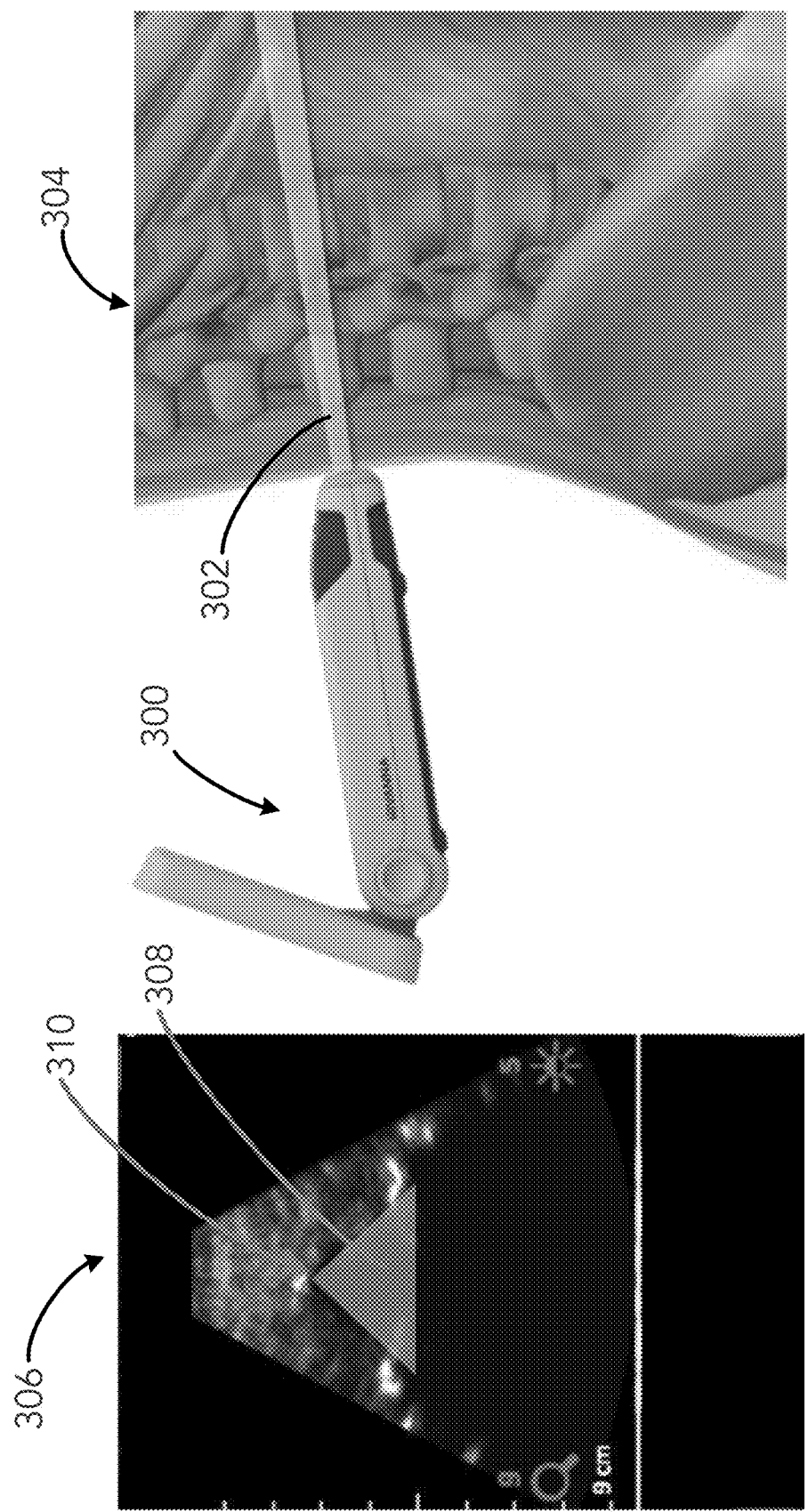
FIG. 3 depicts an exemplary ultrasound beam intersecting a spinous process and illustrates a visualization of a 2D ultrasound image of an imaged area together with a 3D model of a transverse cross-section appearing as a triangle, in accordance with some embodiments of the disclosure provided herein.

FIG. 3 depicts an exemplary device 300 projecting an exemplary ultrasound beam 302 intersecting a spinous process of a human spine 304 and illustrates a visualization of a 2D ultrasound image 306 (sometimes referred to as ultrasonogram 306 or ultrsonography 306) of an imaged area together with a triangle overlay 308 disposed on top of a triangular shaped acoustic shadow (covered by the triangle overlay 308 in FIG. 3) in the ultrasound image 306, in accordance with some embodiments of the disclosure provided herein. As such, FIG. 3 demonstrates how an exemplary device is used in practice, in at least some embodiments.

In practice, in at least some embodiments, the device 300 can be moved longitudinally along the spine 304. In at least some embodiments, the ultrasonic beam 302 projects substantially coaxially with the device 300. In at least some embodiments, the device's ultrasonic transducers are arranged transversely relative to the spine 304 (orthogonally to the page of FIG. 3 right). This gives rise to the ultrasonogram 306 illustrated in FIG. 3. Those skilled in the art might appreciate and recognize the triangular shape of the acoustic shadow (covered by the triangle overlay 308) whose boundaries represent the spinous process (represented at the top 310 of the triangle overlay) and the articular process (represented at the two bottom corners 312, 314 of the triangle overlay).

Figure 4:
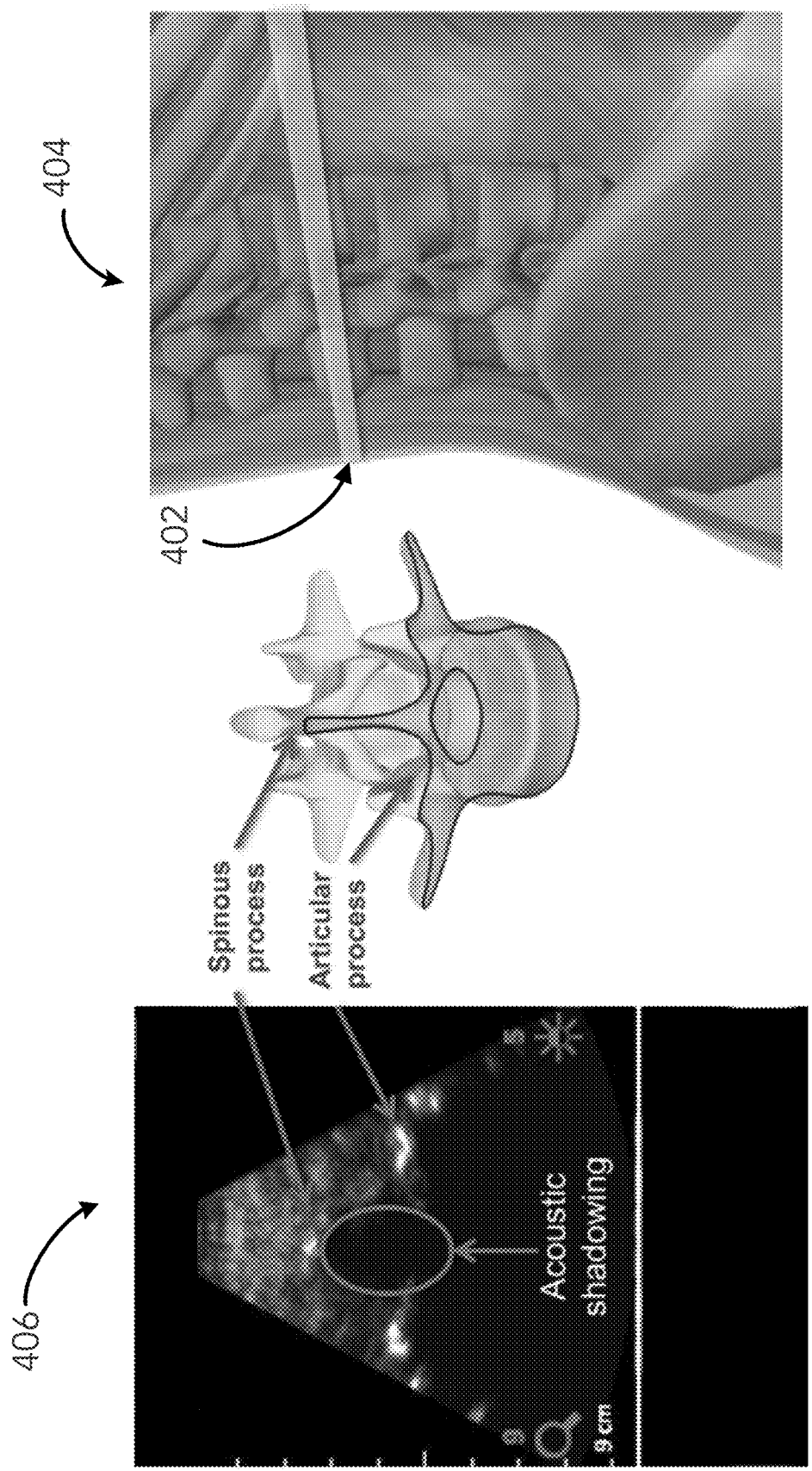
FIG. 4 depicts an exemplary ultrasound beam intersecting a spinous process and illustrates a visualization of a 2D ultrasound image of an imaged area together with a 3D model of a transverse cross-section exemplifying acoustic shadowing, in accordance with some embodiments of the disclosure provided herein.

FIG. 4 depicts an exemplary ultrasound beam 402 intersecting a spinous process of a human spine 404 and illustrates a visualization of a 2D ultrasound image 406 (which includes acoustic shadowing 408 similar to that covered by the triangle overlay 308 in FIG. 3) of an imaged area of the spine 404 together with a 3D model 410 of a transverse cross-section of the spine 404 that was imaged and resulted in the acoustic shadowing, in accordance with some embodiments of the disclosure provided herein.

Those skilled in the art might appreciate and recognize the triangular shape of the transverse cross section of the spine 404, which results in the triangular shaped acoustic shadow covered by the triangle overlay 308 in FIG. 3.

Now that the transverse cross-sectional triangle has been properly identified and associated with the spinal anatomy 304 (FIG. 3), 404 and 410, the underlying acoustic shadowing 408 and pertinence thereof with respect to the present invention will now be discussed in greater detail.

Figure 5:
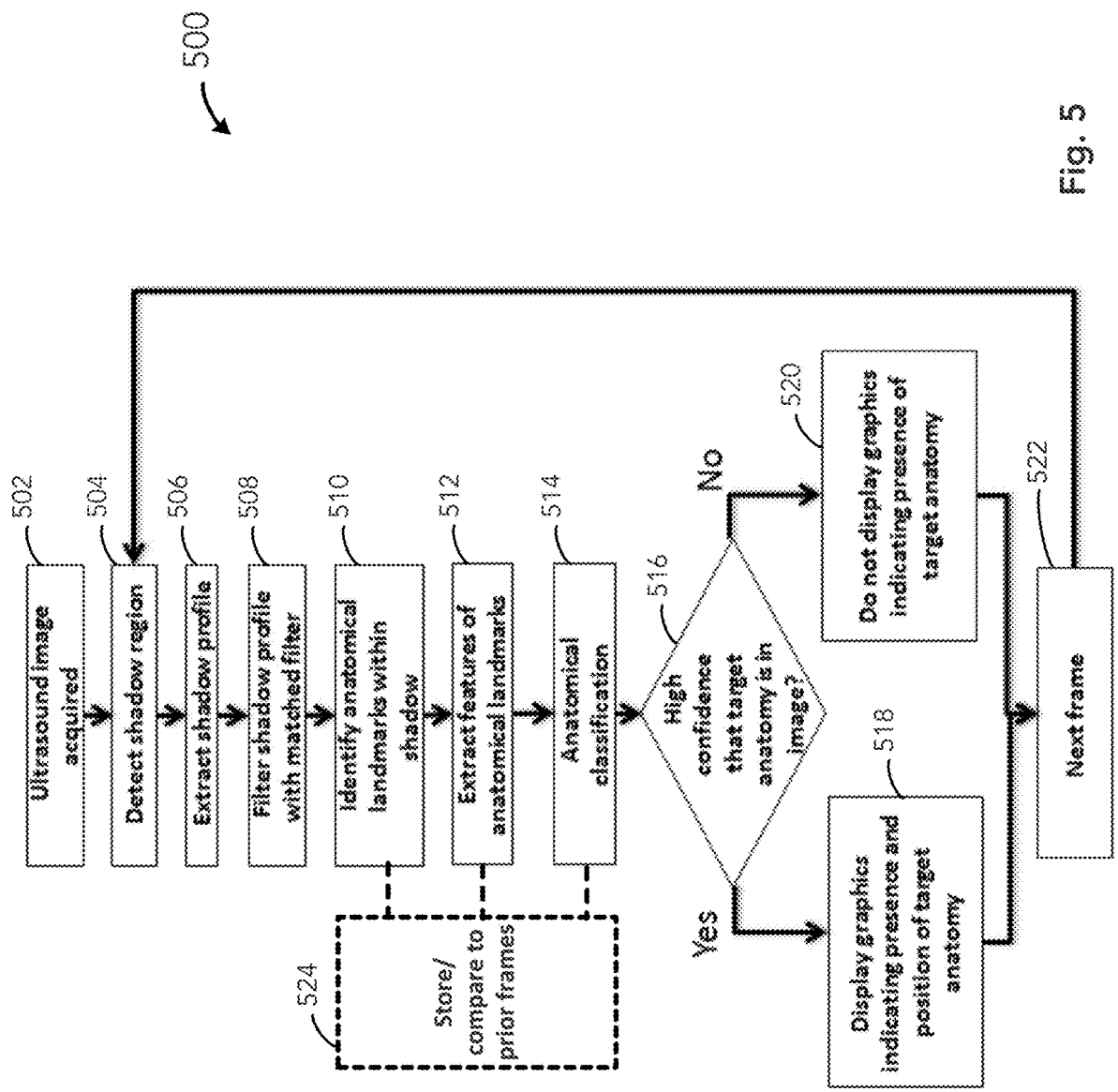
FIG. 5 is a flowchart of an illustrative process of generating a visualization of a 2D ultrasound image and corresponding cross-section of a 3D bone model and anatomy identification, in accordance with some embodiments of the disclosure provided herein.

FIG. 5 is a flowchart 500 of an illustrative process (method) of generating a visualization of a 2D ultrasound image and corresponding cross-section of a 3D bone model and anatomy identification, in accordance with some embodiments of the disclosure provided herein. The flowchart 500 provides a broad overview of the process, which includes a process referred to herein as acoustic shadowing for sonoanatomy. Each step and some sub-steps in the process will be discussed in detail.

Briefly, however, and in accordance with at least some embodiments, a shadow (sometimes referred to herein as an acoustic shadow) is identified in an ultrasound image (sometimes referred to herein as a frame). In at least some embodiments, the shadow is identified in each image of a series of images (frames), sometimes referred to herein as identification on a frame by frame or per frame basis. In at least some embodiments, a feature extraction method is performed on the identified shadow to identify the presence or absence of a set of (one or more) anatomical features. In at least some embodiments, the feature extraction method includes a matched filter that measures similarity between the acoustic shadow and an anticipated acoustic shadow, which in at least some embodiments, is predicted from a profile of a target anatomy, e.g., spinous process. In some embodiments, a user specifies the target anatomy. In some other embodiments, information regarding the target anatomy is received from one or more other sources (external and/or internal). In at least some embodiments, the shadow information is sufficient from which to classify an anatomy in an ultrasound image as one of the following: epidural space, spinous process, sacrum, spine midline, boney anatomy, lung and/or trachea. In at least some embodiments, the presence and/or position (for example, depth, lateral position, rotation, etc.) of one or more anatomical features (e.g., spinous process, epidural spaces, etc.) are detected via a set of peak detection, zero-crossing, and/or other operation(s) on the shadow data and, in at least some embodiments, are provided to the user via a graphic user interface on a hand held device being used to perform the ultrasound and/or via a graphic user interface on some other device. In some embodiments, the information that is provided to a user via the graphical user interface may include: location of spinous process(es), location of epidural space(s), location of spine midline, location of sacrum, depth to spinous process tip, depth to epidural space and/or angular rotation of spine. In some embodiments, the method may be used to distinguish placement of an intubation tube in the trachea or esophagus.

Referring now to FIG. 5, in accordance with some embodiments, the method may comprise the following steps: acquiring ultrasound image (step 502); detecting shadow region (step 504); extracting shadow profile (step 506); filtering shadow profile with matched filter (step 508); identifying anatomical landmarks within shadow (step 510); extracting features of anatomical landmarks (step 512); classifying anatomy (step 514), and determining whether there is a high degree of confidence that the target anatomy is depicted in the image (step 516).

If at 516 it is determined that there is a high degree of confidence, the method proceeds with a step 518 of displaying graphics indicating a presence and/or a position of target anatomy. If at 516 a high degree of confidence is not determined, the method proceeds by not displaying graphics indicating the presence of target anatomy (step 520). Upon the execution of either conditional step (518 or 520), the method continues to the next frame (for analysis) (step 522) and restarts the process at the step 504 of detecting shadow region.

In an embodiment, the system and method include a modality and steps for storage of data and results of the analysis of data, for example, for storing a prior detected or extracted or classified object (e.g., at 524). In particular, in a multi-frame sequence, the analysis or classification of an object (e.g., a spinous process shadow) in a frame of the sequence can be compared to one or more prior sequences (e.g., at 524) to confirm that the object was also found in said prior sequences. If this is the case, that result affirms the location or classification of the object in the latter frames. This affirmation can further enhance the degree of confidence in the detection and classification process.

It should be appreciated that the presently provided examples, systems, and methods are not necessarily exhaustive of the embodiments and features of the invention, all of which are comprehended hereby. However, some preferred embodiments and illustrative aspects are provided in these examples. The steps recited in the examples provided may be complemented with other steps or sub-processes, substituted with equivalent or similar steps, or re-arranged to suit a given application. The same is true for the illustrative systems and apparatus embodiments where other equally applicable examples could occur to those skilled in the art upon review of the present disclosure, and where substitutions, additions or deletions of some elements may not depart from the scope of this disclosure.

Figure 6:
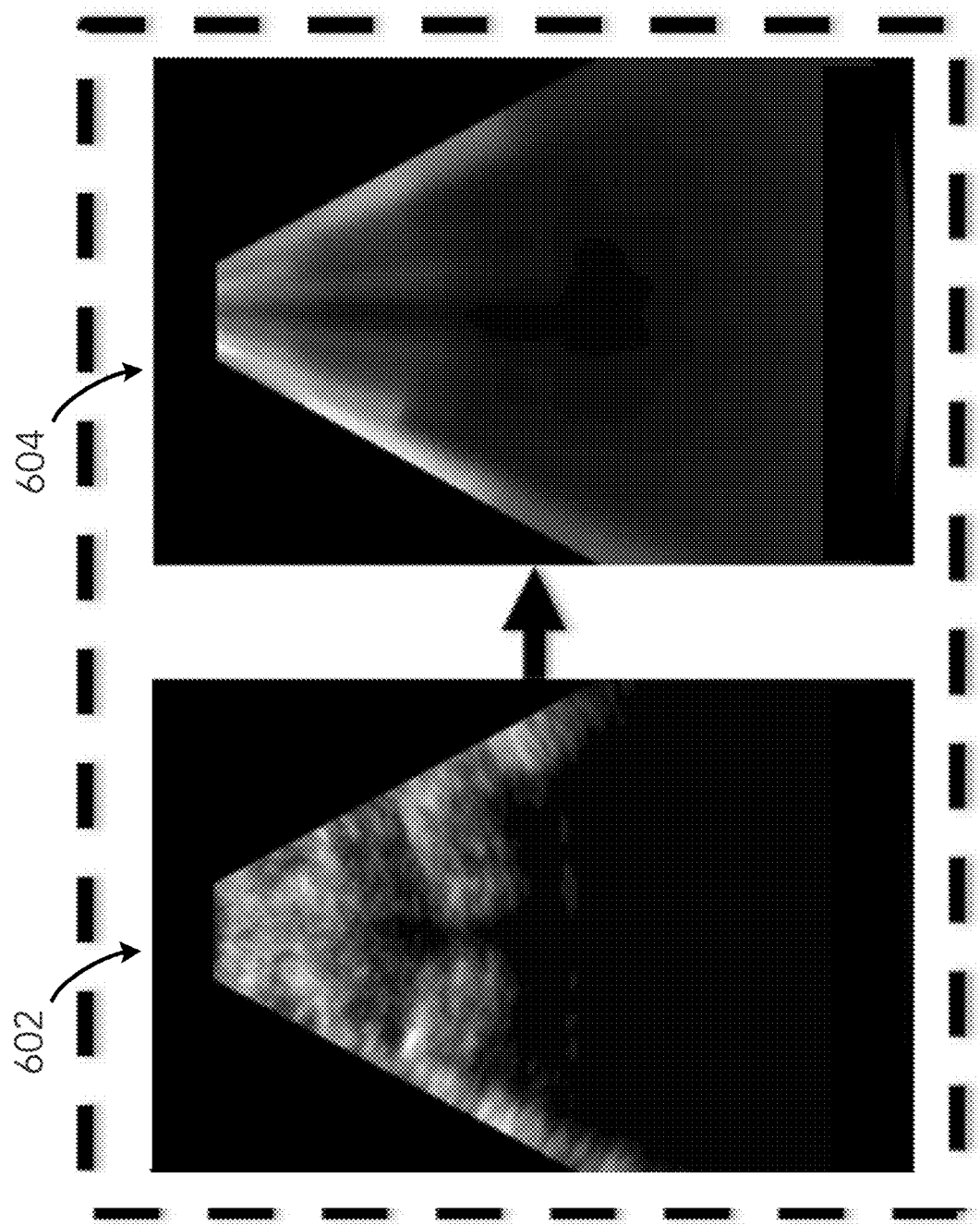
FIG. 6 illustrates the application of the imaging techniques and initial steps of processing the acoustic shadowing method described herein for the purpose of sonoanatomy, in accordance with some embodiments of the disclosure provided herein.

FIG. 6 illustrates the application of imaging techniques and initial steps of processing that may be performed at step 502 ("ultrasound image acquired") in the flowchart 500 (FIG. 5) and at step 504 ("detect shadow region") in the flowchart 500 (FIG. 5), in the acoustic shadowing method described herein for the purpose of sonoanatomy, in accordance with some embodiments of the disclosure provided herein.

In particular, FIG. 6 shows a visualization 602 of harmonic frequency data in an ultrasound image that may be acquired at step 502 ("ultrasound image acquired") and a visualization 604 of an image (sometimes referred to herein as a "shadow image") that may be generated based at least in part thereon at step 504.

In one or more embodiments, step 502 ("ultrasound image acquired") and step 504 ("detect shadow region") are carried out using a method that comprises: using at least one computer hardware processor to obtain ultrasound data generated based, at least in part, on one or more ultrasound signals from an imaged region of a subject. The ultrasound data comprises fundamental frequency ultrasound data and harmonic frequency ultrasound data. Note that, as mentioned above, the ultrasound image 602 shown in FIG. 6 includes the harmonics of the fundamental frequency but not the fundamental frequency data (which has been removed by filtering and/or other processing) and is therefore sometimes referred to herein as a "harmonic image". In some embodiments, the method further comprises: performing shadow detection based at least in part on the harmonic frequency ultrasound data. This may comprise: calculating shadow intensity data based at least in part on the harmonic frequency ultrasound data and generating, based at least in part on the fundamental frequency ultrasound data, an indication of bone presence in the imaged region. In some embodiments, the method includes generating, based at least in part on the shadow intensity data, an indication of tissue presence in the imaged region, and generating an ultrasound image of the subject at least in part by combining the indication of bone presence and the indication of tissue presence.

In some embodiments, the method may comprise enhancing bone contrast by using the reciprocal of a shadow intensity value at every pixel location in an ultrasound image, where the shadow intensity value may be defined as:

$$S(i, j) = \sum_{k=i+\alpha}^{M} w_{k,i} I(k, j) S(i, j) = \sum_{k=i+\alpha}^{M} w_k I(k, j)$$

wherein, $S(i,j)$ is the shadow intensity output, $I(i,j)$ is the envelope detected ultrasound image data, $w_k$ is a depth weighting, and $\alpha$ is an offset. The indices i range from 1 through the M number of depth samples in I. The index j ranges from 1 through the N number of scan lines. The weighting values $w_{k,i}$ are typically constant with k and chosen as a function only of i such that the output $S(i,j)$ corresponds to the average envelope detected values in column j from $i+\alpha$ through M. However, in other embodiments the weightings may be variable such as to be more or less sensitive to pixel locations further or closer to the current pixel location k, j.

In some embodiments, the offset $\alpha$ is determined as the thickness in the range, or depth, dimension of a bone surface in the envelope detected ultrasound data. In this way, if pixel depth location i corresponds to a bone surface point, then the shadow intensity output sums only over regions of signal dropout (i.e. shadow) rather than incorporating signal from bone. That is to say, if pixel depth location i were located at the leading, most shallow, edge of a bone surface, then pixel locations i through $i+(\alpha-1)$ are comprised of signal from the bone surface while $i+\alpha$ through M locations are comprised of shadow only. The exact value of $\alpha$ may be determined by experimental observation or derived from the axial resolution of the imaging system.

The output of the bone filter may then be calculated as the pointwise division of the envelope detected ultrasound image with the shadow intensity values with an additional factor, $\tau$, which is chosen as a small number in order to avoid division by 0.

$$B(i,j) = I(i,j)/(S(i,j)+\tau) \quad (1)$$

It should be appreciated that the bone filter output may be formed using a function other than a pointwise-division as described with respect to Equation 1. For example, a sigmoidal function may be used.

A complete description of the method (and application thereof) that may be used, in whole or in part, at step 504 ("detect shadow region") in the flowchart 500 (FIG. 5) is found in U.S. patent application Ser. No. 15/044,425 entitled, "System and Method for Ultrasound Imaging of Regions Containing Bone Structure" filed on 16 Feb. 2016, which is hereby incorporated by reference in its entirety.

In at least some embodiments, the shadow (sometimes referred to herein as the acoustic shadow) is identified on a per-frame basis.

After step 504 ("detect shadow region") of flowchart 500 (FIG. 5), processing may proceed to step 506 ("extract shadow profile").

Figure 7:
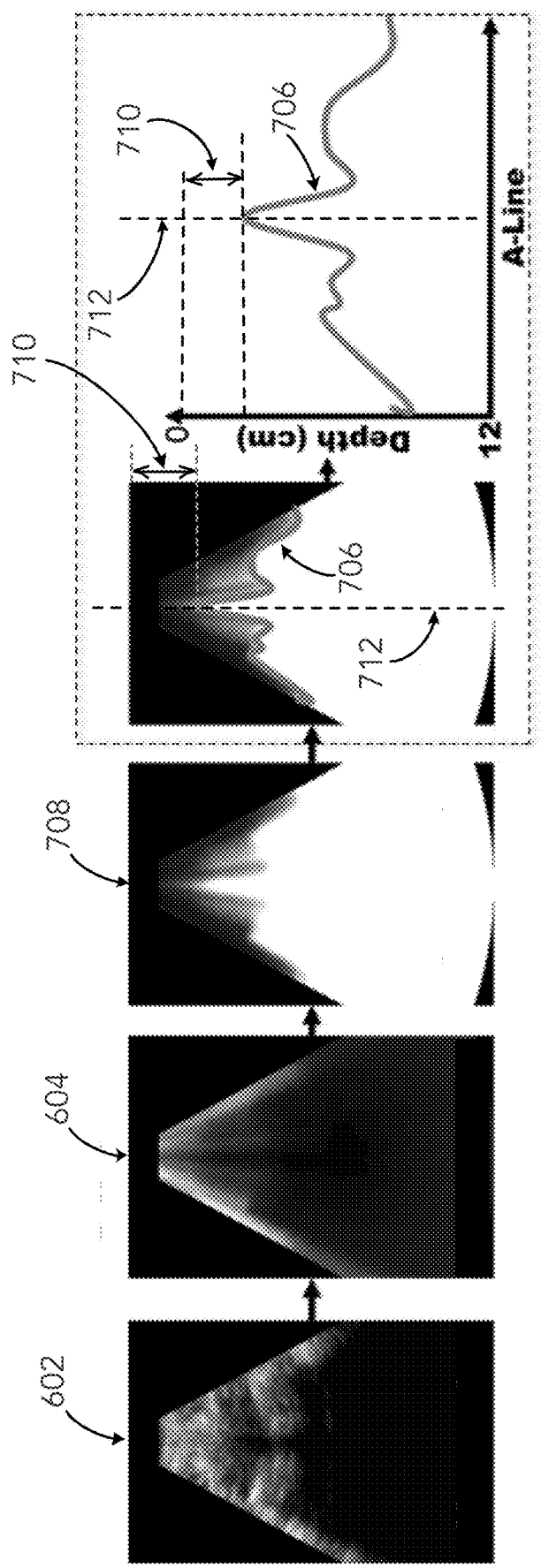
FIG. 7 illustrates the application of the imaging techniques and subsequent steps of processing the acoustic shadowing method described herein for the purpose of sonoanatomy, in accordance with some embodiments of the disclosure provided herein.

FIG. 7 illustrates the application of the imaging techniques and the initial processing steps illustrated in FIG. 6, as well as subsequent steps of processing that may be performed at and/or otherwise in association with step 506 ("extract shadow profile") of flowchart 500 (FIG. 5), in the acoustic shadowing method described herein for the purpose of sonoanatomy, in accordance with some embodiments of the disclosure provided herein.

Referring to FIG. 7, after ultrasonic imaging 602 and shadow filtering or otherwise to detect the shadow 604 from the harmonic, a shadow profile 706 is extracted therefrom. In accordance with at least some embodiments, the shadow profile 706 constitutes the boundary between soft tissue and shadow within the ultrasound image. In some embodiments, the shadow profile is extracted by nonlinear processing of the shadow image or a reciprocal 708 (sometimes referred to herein as an inverse) of the shadow image. In some embodiments, the extraction of the shadow profile may be carried out A-Line by A-Line, by determining a depth at which the shadow begins in each A-Line (e.g., depth 710 in A-Line 712) and defining the value of the shadow profile in each A-Line as the depth (or a value based at least in part thereon) at which the shadow begins in that A-line. Those skilled in the art will appreciated that the most superficial peak in the center of the shadow profile corresponds to the spinous process in the current exemplary embodiment.

A shadow profile is not limited to the shadow profile shown in FIG. 7. Nor are methods for determining a shadow profile limited to the methods described above. A shadow profile may have any suitable form(s) and may be determined using any suitable method(s). For example, in view of the disclosure herein, at least in part, those skilled in the art will recognize that one or more shadow profiles can be extracted from a shadow image or directly from ultrasound image data through various standard image processing methods including edge detection, contour mapping, template matching, or machine learning. Those skilled in the art will also recognize that the shadow profile represents the location of a boundary between the shadow region and tissue and may take the form of a one-dimensional vector, two-dimensional polygon, or three-dimensional surface.

After step 506 ("extract shadow profile") of flowchart 500 (FIG. 5), processing may proceed to step 508 ("filter shadow profile with matched filter"). At step 508 ("filter shadow profile with matched filter") the extracted shadow profile 706 may be convolved with a matched filter.

Figure 8:
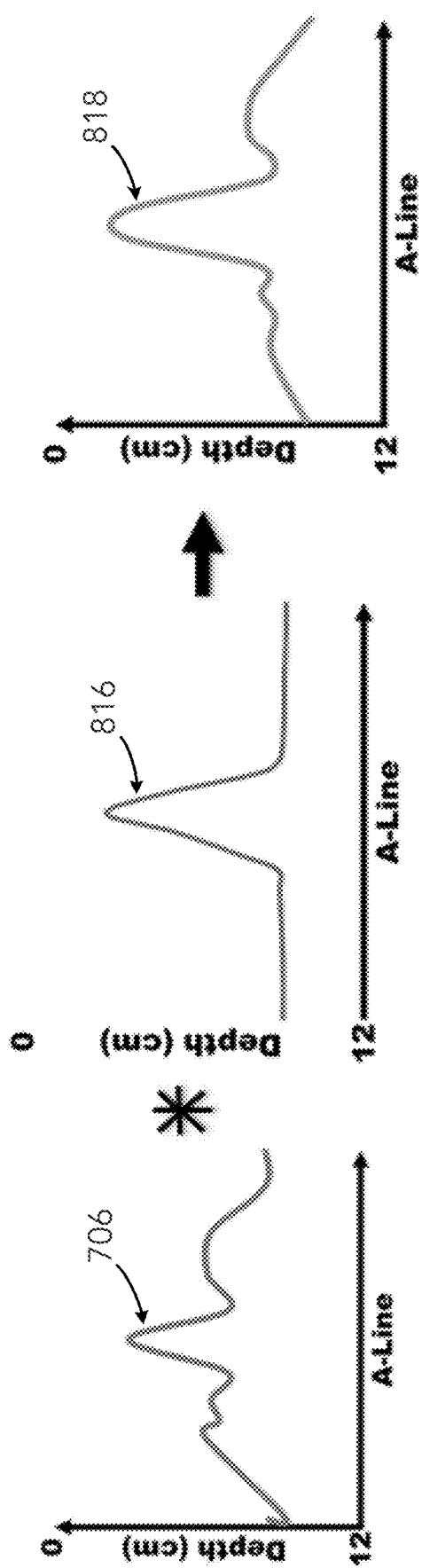
FIG. 8 depicts the convolution of an extracted acoustic shadowing profile with an exemplary matched filter resulting in an exemplary filtered shadow profile, in accordance with some embodiments of the disclosure provided herein.

FIG. 8 depicts a convolution of an extracted acoustic shadowing profile 706 with an exemplary matched filter 816 resulting in an exemplary filtered shadow profile 818, in accordance with some embodiments of the disclosure provided herein.

Similar to cross-correlation, convolution is a mathematical operation on two functions (f and g) and produces a third function. The resultant third function (i.e., f and g convolved) is typically viewed as a modified version of one of the original functions, giving the integral of the pointwise multiplication of the two functions as a function of the amount that one of the original functions is translated.

Convolution can be defined for functions on groups other than Euclidean space. For example, periodic functions, such as the discrete-time Fourier transform, can be defined on a circle and convolved by periodic convolution. A discrete convolution can be defined for functions on the set of integers. Generalizations of convolution have applications in the field of numerical analysis and numerical linear algebra, and in the design and implementation of finite impulse response filters in signal processing.

In reference to FIG. 8, each graph approximates functions on two axes. The A-Line on the horizontal axis corresponds to the transverse cross section, while the vertical axis measures the depth in cm of the A-Line profile at that location. The shadow profile 706 which in at least some embodiments, was extracted in a manner discussed in association with FIG. 7, is convolved with a matched filter 816 that approximates an expected shadow profile of a target anatomy. In the present example, the target anatomy is a spinous process, which casts a shadow with one prominent peak.

In the present exemplary embodiment, the matched filter is an idealized filter, such as a Gaussian profile. In some other embodiments, the matched filter is a function that is derived from or otherwise based at least in part on shadow profiles measured from multiple human datasets. In some embodiments, multiple matched filters are convolved with the shadow profile so as to quantify similarity to different anatomical structures. In the preferred embodiment, the matched filter substantially resembles the anticipated anatomical structure thereby giving rise to the most useful and accurate convolution. However, other functions, such as, sincs, low-pass filtered impulses (delta) or higher order smoothing functions are not beyond the scope of the present invention.

The resultant of the convolution is sometimes referred to herein as a filtered shadow profile, e.g., the filtered shadow profile 818.

After step 508 ("filter shadow profile with matched filter") of flowchart 500 (FIG. 5), processing may proceed to the step 510 ("identify anatomical landmarks within shadow") of the flowchart 500 (FIG. 5), in which identification of anatomical landmarks within the filtered shadow profile may be performed.

FIG. 9A is a flowchart 900 of sub-steps that may be executed in association with the step 510 ("identifying anatomical landmarks within shadow") in the flowchart 500 (FIG. 5), in accordance with some embodiments.

Referring to FIG. 9A, in accordance with some embodiments, the sub-steps performed at step 510 ("identify anatomical landmarks within shadow") may include: detecting peaks (or one or more other features) on shadow profile (sub-step 902); selecting subset of most prominent peaks (or a subset of the one or more other features) (sub-step 904); and, classifying peaks (or other subset) as anatomical features (e.g., midline, spinous process, lamina, articular process, etc.) (sub-step 906).

FIG. 9B depicts a convolved exemplary filtered shadow profile 818 and the application of peak detection thereto 920 (e.g., as performed at sub-steps 902-906 of the flowchart 900) for the purpose of sonoanatomy, in accordance with some embodiments of the disclosure provided herein.

Referring to FIG. 9B, peak detection 920 has been performed on the filtered shadow profile 818 to identify the most prominent peaks based at least in part on the filtered shadow profile 818. In accordance with some embodiments, this involved performance of sub-step 902 to detect peaks on the filtered shadow profile 818 and sub-step 904 to select a subset of the most prominent peaks. In the illustrated embodiment, four peaks, i.e., peaks 922-928, have been selected as the most prominent peaks.

At sub-step 906, the most prominent peaks are classified as anatomical features (e.g., midline, spinous process, lamina, articular process, etc.) (step 906). In some embodiments, when imaging in the transverse orientation as in the present exemplary embodiment, it is assumed that the most superficial (prominent) peak corresponds to the tip of the spinous process and that the lower (prominent but less prominent than the most prominent) peaks correspond to the lamina/articular processes.

Thus, in some embodiments, the most prominent peak, e.g., peak 922, is classified as corresponding to a tip of spinous process. The other most prominent peaks, e.g., peaks 924, 926, 928, which are less prominent than the most prominent peak, are classified as corresponding to peaks of lamina and/or articular processes.

In some other embodiments, the most prominent peak (or another feature) may be classified as corresponding to another anatomical feature, e.g., a peak (or other portion) of a first anatomical feature. Other prominent peaks (or other prominent features) may be classified as corresponding to other anatomical features, e.g., a peak (or other portion) of a second anatomical feature, a peak (or other portion) of a third anatomical feature, a peak (or other portion) of a fourth anatomical feature, etc. Thus, in some embodiments, one or more other peaks and/or one or more features other than a peak or peaks may be detected and/or classified as corresponding to anatomical features.

After step 510 ("identify anatomical landmarks within shadow") of flowchart 500 (FIG. 5), processing may proceed to step 512 ("extract features of anatomical landmarks") in which extraction of anatomical landmarks within the filtered shadow profile may be performed.

Figure 10A:
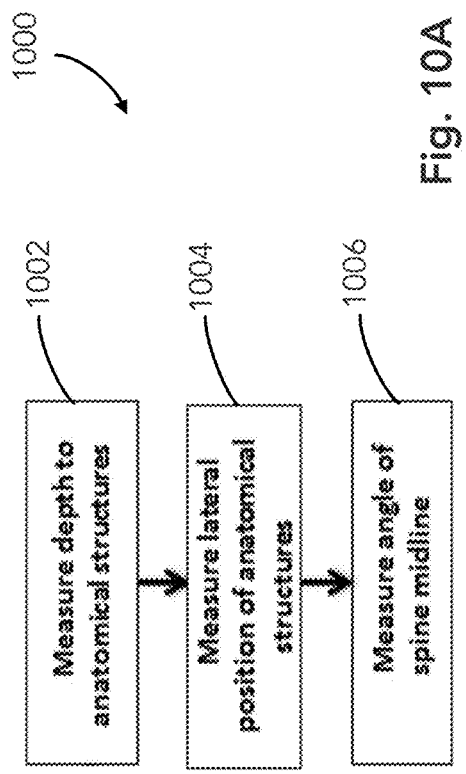
FIG. 10A is a flowchart of a method, in accordance with some embodiments.

FIG. 10A is a flowchart 1000 of sub-steps that may be executed in association with the step 512 ("extract anatomical landmarks") in the flowchart 500 (FIG. 5), in accordance with some embodiments.

Figure 10B:
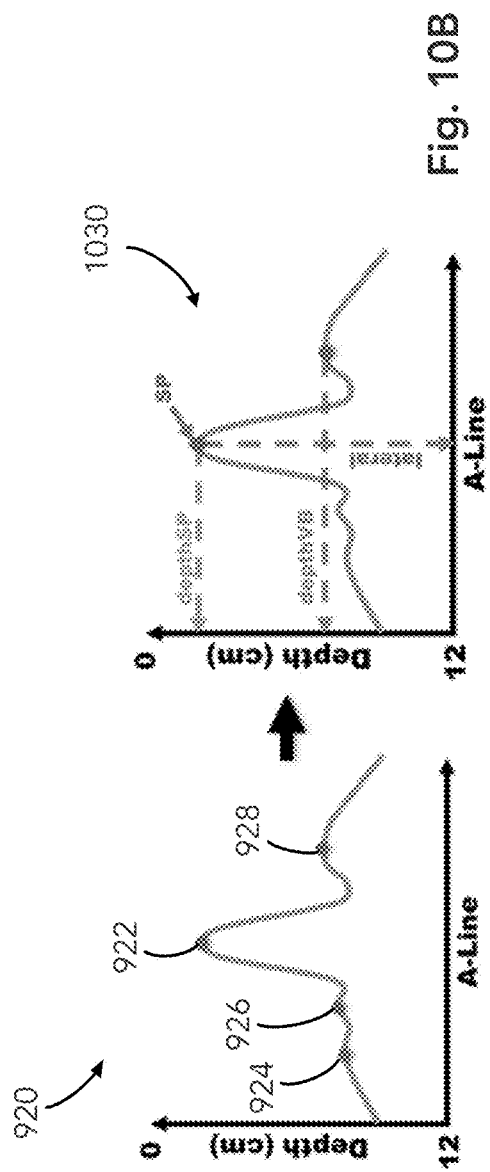
FIG. 10B depicts a convolved exemplary filtered shadow profile, the application of peak detection thereto and extraction of associated metrics for the purpose of sonoanatomy, in accordance with some embodiments of the disclosure provided herein.

Referring to FIG. 10A, in accordance with some embodiments, the sub-steps performed at step 512 of the flowchart 500 may include: measuring depth to anatomical structures (sub-step 1002); measuring lateral position of anatomical structures (sub-step 1004); and, measuring angle of spline midline (sub-step 1006). FIG. 10B depicts a convolved exemplary filtered shadow profile (e.g., filtered shadow profile 818), the application of peak detection 920 thereto and extraction of associated metrics 1030 (e.g., as performed at sub-steps 1002-1006 of the flowchart 1000), for the purpose of sonoanatomy, in accordance with some embodiments of the disclosure provided herein.

As stated above in regard to FIGS. 9A-9B, the peaks, e.g., peaks 922-928, that were detected in the sub-steps 902-906 were associated with FIGS. 9A-9B correspond to anatomical structures.

Referring to FIG. 10B, extraction of metrics 1030 has been performed in accordance with some embodiments.

In the present embodiment, the depth of two of the anatomical structures, i.e., anatomical structures corresponding to peaks 922, 928, have been measured or otherwise determined, and the lateral position of one of the anatomical structures has been measured or otherwise determined. In accordance with some embodiments, this involved performance of sub-step 1002 to measure or otherwise determine the depth of the two anatomical structures.

The measured or otherwise determined depths are identified by reference labels depthSP and depthVB, respectively. That is, depthSP of FIG. 10B is a measure of the depth of the peak 922, which in the illustrated embodiment, is a measure of the depth of the tip of the spinous process from the epidermis surface. DepthVB of FIG. 10B is a measure of the depth of the peak 928, which in the illustrated embodiment, is a measure of the depth of a vertebral body from the epidermis surface.

Sub-step 1004 ("measure lateral position of anatomical structures") has been performed to measure or otherwise determine the lateral position of one of the anatomical structures.

The measured or otherwise determined lateral position is identified by reference label "lateral" of FIG. 10B, which is a measure of the lateral position of peak 922, which in the illustrated embodiment, is a measure of the lateral position of the spinous process. In at least some embodiments, the lateral position is determined as a measure of the transverse displacement of the peak, e.g., peak 922, which in the illustrated embodiment is a measure of the transverse displacement of the tip of the spinous process, along the A-Line in which such peak (corresponding anatomical structure) is disposed.

Sub-step 1006 ("measure angle of spline midline") may be performed to measure or otherwise determine an angle of a spline midline.

Figure 11:
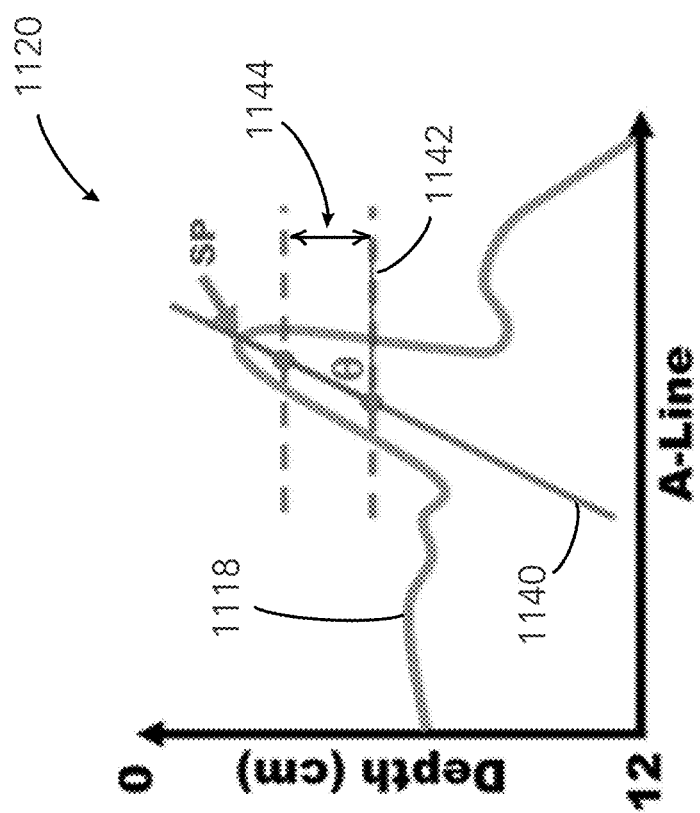
FIG. 11 depicts a convolved exemplary filtered shadow profile, the application of peak detection thereto and extraction of associated metrics, such as, orientation for the purpose of sonoanatomy, in accordance with some embodiments of the disclosure provided herein.

A spline midline and a measurement or other determination of an angle thereof are further discussed with respect to FIG. 11.

FIG. 11 depicts a convolved exemplary filtered shadow profile 1118, the application of peak detection thereto 1120 and extraction of associated metrics, such as, orientation (e.g., which may be determined at sub-step 1006 of the flowchart 1000) for the purpose of sonoanatomy, in accordance with some embodiments of the disclosure provided herein.

It should be recognized that the filtered shadow profile 1118 in FIG. 11 is angularly offset from the filtered shadow profile 818 by an angle θ.

Thus, FIG. 11 illustrates the sub-step 1006 of FIG. 10A (e.g., measuring the angular rotation of the anatomical structure (that is the spinal rotation of the spinous process in the illustrated example)) represented by a filtered shadow profile 1118 that is angularly offset relative to the filtered shadow profile 818 discussed above by an angle θ.

In accordance with at least some embodiments, sub-step 1006 comprises: determining a midline (or other line(s) or curve(s)) using one or more spline (and/or other function(s) (interpolation or otherwise)) and measuring or otherwise determining an angular offset of the determined midline (or other line or curve) with respect to one or more references within one or more ranges. In at least some embodiments, the midline (or other line(s) or curve(s)) will include the most prominent peak, e.g., peak SP, or one of the other peaks (and thus the anatomical structure corresponding thereto). In at least some embodiments, the one or more references will include a reference parallel to: an axis and/or edge of the ultrasound image.

In the illustrated embodiment, a spline midline 1140 has been determined. An angle θ of the spline midline 1140 (relative to a reference 1142 within a range 1144) has also been determined.

After step 512 ("extract features of anatomical landmarks") of flowchart 500 (FIG. 5), processing may proceed to step 514 ("classify anatomy") in which classification of anatomical landmarks within the filtered shadow profile may be performed.

FIG. 12A is a flowchart 1200 of sub-steps that may be executed in association with the step 514 ("classifying anatomy") in the flowchart 500 (FIG. 5), in accordance with some embodiments.

Referring to FIG. 12A, in accordance with some embodiments, the sub-steps performed at step 514 of the flowchart 500 may include: calculating confidence/classification metric (sub-step 1202); classifying anatomy as containing target anatomy or not (sub-step 1204); and, determining accuracy of anatomical measurements computed in step 512 of flowchart 500 (FIG. 5) based on confidence metric (sub-step 1206). In some embodiments, one or more of sub-steps 1202-1206 may be used in determining whether a spinous process an epidural space and/or other anatomical structures are actually present in an image.

FIG. 12B depicts a convolved exemplary filtered shadow profile 818, the application of peak detection 920 thereto and extraction of associated metrics 1240, 1250 based at least in part thereon (e.g., as performed at one or more of sub-steps 1202-1206 of the flowchart 1200) for the purpose of sonoanatomy, in accordance with some embodiments of the disclosure provided herein.

In accordance with at least some embodiments, sub-steps 1202-1206 comprise: measuring or otherwise determining a height (and/or other characteristic(s)) of a spinous process (and/or other (e.g., expected) anatomical feature(s)); and determining a metric that is indicative of a confidence level that a spinous process (and/or other (e.g., expected) anatomical feature(s)) is in the ultrasound image based at least in part on the determined height (and/or other characteristic(s)) of the spinous process (and/or other (e.g., expected) anatomical feature(s).

In some embodiments, measuring or otherwise determining the height of a spinous process comprises: determining a depth from a peak of a spinous process to a peak of a side lobe; determining a depth of a side lobe; defining a height of the spinous process as a difference between (or otherwise based at least in part on) the two depths.

In some embodiments, determining a metric that is indicative of a confidence level that a spinous process (and/or other (e.g., expected) anatomical feature(s)) is in the ultrasound image comprises: determining a metric indicative of a level of confidence based at least in part on the height or difference (or other metric) and one or more criteria. In some embodiments, the latter comprises comparing the difference to one or more reference values.

Thus, in some embodiments, the height of the spinous process is determined as the difference in the depths of the "Peak" and "Side Lobe" as shown in metrics 1240 (FIG. 12B) generated for a shadow profile of a spinous process. Computing a peak-to-side-lobe ratio returns a metric between 0.0 and 1.0. The peak-to-side-lobe ratio may be used to determine if a spinous process is disposed in the ultrasonic image. In some embodiments, if the peak-to-side-lobe ratio is close to 1.0, then a determination is made that a spinous process is present. In some embodiments, ratios that are "close to 1.0" includes ratios that are greater than 0.75. Ratios ranging from 0.50 to 0.75 may or may not be included. In some embodiments, ratios greater than 0.50 are included. In some embodiments, ratios less than 0.75 are excluded. In some embodiments, if the peak-to-side-lobe ratio is closer to 0.0, then a determination is made that a spinous process is not present. In some embodiments, ratios that are "closer to 0.0" includes ratios that are less than 0.25. Ratios ranging from 0.26 to 0.74 may or may not be included. In some embodiments, ratios less than 0.49 are included. In some embodiments, ratios greater than 0.5 are excluded. In some embodiments, the peak-to-side-lobe ratio is used both as a classifier and as an indicator in the confidence of the anatomical metrics extracted in step 512 ("extract features of anatomical landmarks") of the flowchart 500 (FIG. 5).

In some embodiments, a determination may additionally or alternatively be made as to whether or not an epidural space is present. In some embodiments, a "Peak" and a "Side Lobe" depth are determined as shown in metrics 1250 (FIG. 12B) generated for a shadow profile of epidural space. Computing a peak-to-side-lobe ratio returns a metric between 0.0 and 1.0. The peak-to-side-lobe ratio may be used to determine if an epidural space is disposed in the ultrasonic image. In some embodiments, if the peak-to-side-lobe ratio is close to 0.0, then a determination is made that an epidural space is present. In some embodiments, ratios that are "close to 0.0" includes ratios that are less than 0.05. Ratios ranging from 0.05 to 0.1 may or may not be included. In some embodiments, ratios less than 0.10 are included. In some embodiments, ratios greater than 0.2 are excluded. In some embodiments, if the peak-to-side-lobe ratio is closer to 1.0, then a determination is made that an epidural space is not present. In some embodiments, ratios that are "closer to 1.0" includes ratios that are greater than 0.25. In some embodiments, the peak-to-side-lobe ratio is used both as a classifier and as an indicator in the confidence of the anatomical metrics extracted in step 512 ("extract features of anatomical landmarks") of the flowchart 500 (FIG. 5).

In some embodiments, one or more portions of step 510 ("identify anatomical landmarks within shadow"), step 512 ("extract features of anatomical landmarks") and/or step 514 ("anatomical classification") may be carried out by and/or comprise: registering at least one 2D ultrasound image to a 3D model of a region comprising bone; and producing a 2D and/or 3D visualization of the region comprising bone wherein the visualization is derived, at least in part, from the registration of the at least one 2D ultrasound image to the 3D model of the spine. In some embodiments registration can be performed by ultrasonically surveying a substantial portion of a patient's spine; performing an acoustic shadowing method to the survey; accessing existing libraries and analyzing its contents with respect to pattern matching to patient's sonogram; and/or loading 3D model from a previously performed scan (e.g., MRI, etc.) of the patient.

In accordance with some embodiments, the ultrasound data described herein may be provided by a handheld ultrasound imager that may perform one or more of the methods disclosed herein and displays a composite image that is based at least in part on the ultrasound data and based at least in part on the classification of the anatomical structure in the image.

Figure 13:
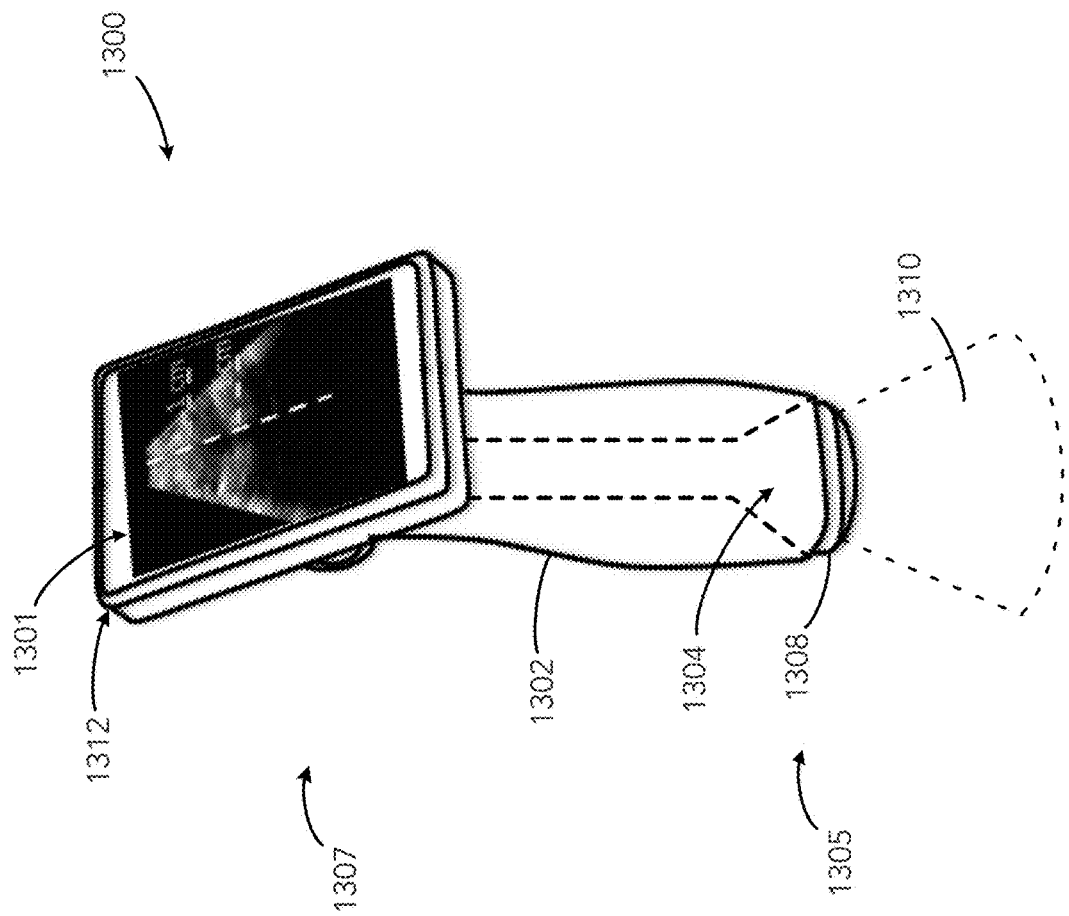
FIG. 13 illustrates an exemplary handheld 2D ultrasound imager with graphical user interface demonstrating probe directional location feedback and non-affixed probe guide together with a 3D model of at least a portion of the imaged area, in accordance with some embodiments of the disclosure provided herein.

FIG. 13 illustrates an exemplary handheld 2D ultrasound imager 1300 with graphical user interface 1301 displaying a view demonstrating one embodiment of a composite image that includes probe directional location feedback and non-affixed probe guide (which may have been generated in part based on a 3D model of at least a portion of the imaged area), in accordance with some embodiments of the disclosure provided herein.

The term "handheld" in the phrase handheld 2D ultrasound imager means that the 2D ultrasound imager is configured to be held in a hand of a user while being used to produce 2D ultrasonic images. Unless stated otherwise, the handheld 2D ultrasound imager is such an imager (a handheld 2D ultrasound imager) even when it is not actually in the hand of a user or other person.

In at least some embodiments, the handheld 2D ultrasound imager 1300 includes a housing 1302 (which may be held in a hand of a user) and an imaging unit 1304, which may be associated with an end 1305 of housing 1302. Imaging unit 1304 may comprise, for example, an ultrasound transducer 1308, which may be configured, in at least some embodiments, to produce an image along at least one scanning plane 1310. In at least some embodiments, the imaging unit 1300 may be configured to produce an image using standard ultrasound image processing techniques known to those of ordinary skill in the art of ultrasound imaging.

The handheld 2D ultrasound imager 1300 comprises, in at least some embodiments, a display 1312 (e.g., an LCD display, an OLED display, or any other suitable type of display), which may display the graphical user interface 1301. In at least some embodiments, the display 1312 may be a located at a second end 1307 of the housing 1302 and/or may be rotatable. In at least some embodiments, ultrasound transducer 1308 may be configured to produce data along at least one scanning plane 1310 that can be subsequently output on display 1312.

In at least some embodiments, the handheld 2D ultrasound imager 1300 with graphical user interface 1301 is a modified version of one or more embodiments of the handheld ultrasound imaging device disclosed in U.S. Patent Application Publication No. 2016/0007956 (of U.S. patent application Ser. No. 14/770,896), entitled "Localization of Imaging Target Regions and Associated Systems and Devices" filed on 27 Aug. 2015, which is hereby incorporated by reference in its entirety, the difference between the handheld 2D ultrasound imager 1300 and the handheld ultrasound imaging device disclosed in U.S. Patent Application Publication No. 2016/0007956 being that the handheld 2D ultrasound imager 1300 includes one or more aspects and/or embodiments of the invention disclosed herein (depending on the application and the features that may be desired for such).

However, the invention is not limited to use with the handheld 2D ultrasound imager 1300 with the graphical user interface 1301 disclosed in FIG. 13. In some embodiments, aspects of the present invention may be employed with different handheld 2D ultrasound imagers.

In at least some embodiments, the composite image will include: (i) a portion that is an ultrasound image and generated based at least in part on the ultrasound data and (ii) a portion that is not part of such ultrasound image and is generated based at least in part on the classification of the anatomical structure. In at least some embodiments, the latter portion may comprise any type of information in any configuration (for example but not limited to graphical and/or textual) that is based at least in part on the classification of the anatomical structure. In some embodiments, the information comprises one or more types of information disclosed herein. In at least some embodiments, the information assists in performance of a medical procedure (other than collection of ultrasound image(s)).

In at least some embodiments, the ability to classify anatomical structures and generate a composite image (e.g., as disclosed herein) for display by a handheld imager (e.g., handheld imager 1300) facilitates a more portable solution for guidance to and/or location of anatomical features which can be operated without extensive training in ultrasonography. In at least some embodiments, such a handheld imager may be simpler to operate than generally available ultrasound imaging equipment. For example, in at least some embodiments, it enables more accurate puncture or probe insertion procedures by providing information to a person viewing the display about a depth and/or location of bone (and/or other structure(s)) with respect to the probe. In at least some embodiments, a handheld imager that displays the composite image is less expensive than generally available B-mode imaging equipment. Also, in at least some embodiments, the composite image disclosed herein provides an intuitive or easy-to-understand indication of a bone location or depth (or other structures and/or details in regard thereto) on a handheld imager, as compared to merely a B-mode sonogram on the handheld imager that can be difficult to interpret. In at least some embodiments, it can also reduce medical costs because the hand-held apparatus can be used for guided probe insertion or anatomical location thereby reducing likelihood of failure or complication during a probe insertion or other medical procedure.

At least some embodiments of the disclosed invention detect both the location of the device location and prospective target anatomy location. A display indicator of target anatomy is presented on a GUI or similar. In some embodiments, an abstraction of the ideal needle path is then portrayed on the display of the GUI. Pursuant to confidence calculation or similar arbiter, a determination is then made to decide whether the target anatomy is centered within the needle path.

If so, an indicator of alignment between the needle path and target anatomy is displayed on the display of the GUI. If non-alignment has been determined, a directional indicator is displayed depicting motion necessary for the ultrasonic device to be centered on the target anatomy. Pursuant to real-time update imaging, next frame loops the process to ensure accuracy.

Indicator symbol designates the direction by which the ultrasound probe needs to translate in order for the target anatomy to align with the prospective needle path. As discussed, GUI indicators can designate necessary motion of the ultrasound probe comprising translation (as shown), compression, or rotation. Indicator symbol, such as yellow dotted line in FIG. 13, denotes that no translation is necessary and the prospective needle path is aligned with the target anatomy.

In some embodiments, an indicator symbol designates rotational by which the ultrasound probe needs to translate in order for the target anatomy to align with the prospective needle path. In other embodiments indicator symbols denote both magnitude and direction. For example, a larger necessary translation might be designated by longer arrow or indicator. In the present embodiment shown in FIG. 13, midline indicators convey relative disposition of the ultrasonic device relative to the loaded template depicting target anatomy and depths of spinous process and/or vertebral body.

Figure 14:
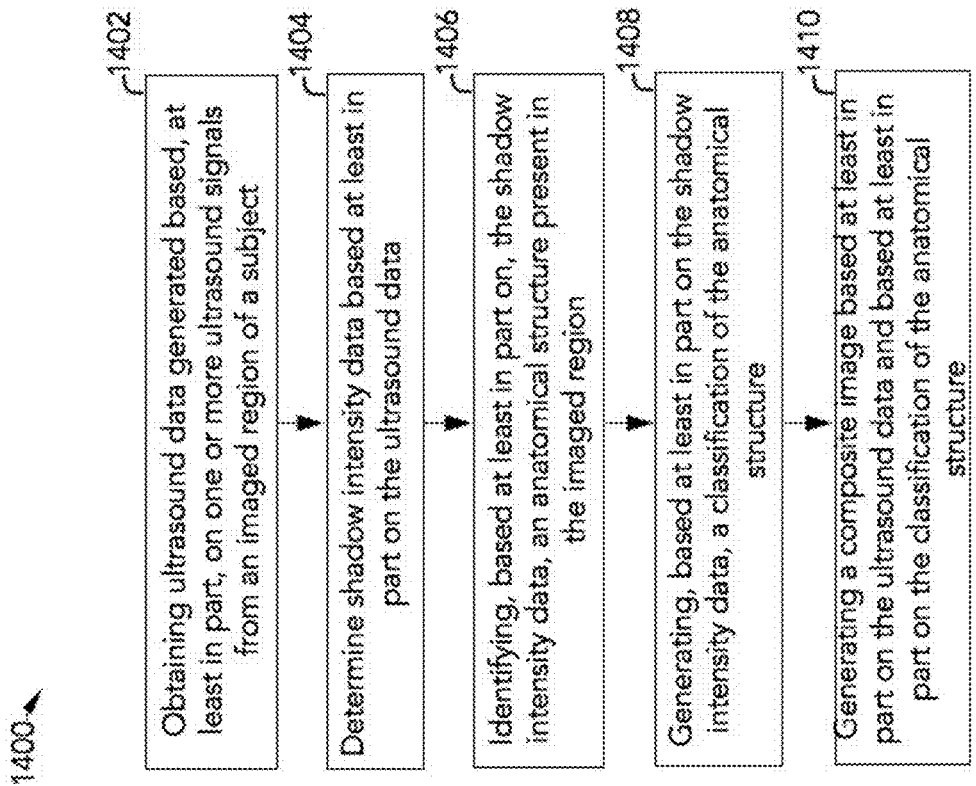
FIG. 14 is a flowchart, in accordance with some embodiments.

FIG. 14 is a flowchart 1400 of a method in accordance with some embodiments. In at least some embodiments, one or more portions of the method may be used without one or more other portions of the method. For that matter, in at least some embodiments, one or more portions of any method disclosed herein may be used without one or more other portions of such method.

In at least some embodiments, the method (or one or more portion(s) thereof) may be used in performance of one or more methods disclosed herein.

In at least some embodiments, the method (or one or more portion(s) thereof) may be performed by the device 1300 (FIG. 13).

Referring now to FIG. 14, at 1402, the method may include obtaining ultrasound data generated based, at least in part, on one or more ultrasound signals from an imaged region of a subject. In at least some embodiments, the ultrasound data may include any type(s) of data in any form(s) from any source(s) (internal and/or external).

At 1404, the method may further include determining shadow intensity data based at least in part on the ultrasound data. In at least some embodiments, this may include one or more of steps 504-506 in flowchart 500 (FIG. 5).

At 1406, the method may further include identifying, based at least in part on the shadow intensity data, an anatomical structure present in the imaged region. In at least some embodiments, this may include one or more of steps 506-512 in flowchart 500 (FIG. 5).

In at least some embodiments, identifying based at least in part on the shadow intensity data may include: filtering the shadow intensity data; performing non-linear processing on the filtered shadow data; and identifying, based at least in part on the non-linearly processed filtered shadow data, an anatomical structure present in the imaged region.

In at least some embodiments, identifying based at least in part on the shadow intensity data may include: determining a shadow profile based at least in part on non-linear processing of the shadow intensity data; and identifying, based at least in part on the shadow profile, an anatomical structure present in the imaged region.

In at least some embodiments, identifying based at least in part on the shadow profile may include: receiving information indicative of a target anatomy; determining an anticipated shadow based at least in part on the information indicative of the target anatomy; determining a measure of similarity between the shadow profile and the anticipated shadow; and identifying, based at least in part on the measure of similarity between the shadow profile and the anticipated shadow, an anatomical structure present in the imaged region.

In at least some embodiments, identifying based at least in part on the shadow profile may include: receiving information indicative of a target anatomy; determining an anticipated shadow based at least in part on the information indicative of the target anatomy; determining a filtered shadow profile based at least in part on a convolution of the shadow profile and the anticipated shadow; and identifying, based at least in part on the filtered shadow profile, an anatomical structure present in the imaged region.

In at least some embodiments, identifying based at least in part on the filtered shadow profile may include: identifying a feature in the filtered shadow profile; and classifying the feature in the filtered shadow profile as a specific anatomical feature.

In at least some embodiments, the identified feature in the filtered shadow profile is a peak in the filtered shadow profile, and the step of classifying the feature as a specific anatomical feature includes: classifying the peak in the filtered shadow profile as a specific anatomical feature.

At 1408, the method may further include generating, based at least in part on the shadow intensity data, a classification of the anatomical structure. In at least some embodiments, this may include one or more of steps 514-520 in flowchart 500 (FIG. 5).

At 1410, the method may further include generating and/or displaying a composite image based at least in part on the ultrasound data and based at least in part on the classification of the anatomical structure. One embodiment of a composite image that may be generated and/or displayed is shown displayed on the display 1312 (FIG. 13) of the imaging device 1300 (FIG. 13).

As stated above, in at least some embodiments, the composite image will include: (i) a portion that is an ultrasound image and generated based at least in part on the ultrasound data and (ii) a portion that is not part of such ultrasound image and is generated based at least in part on the classification of the anatomical structure. In at least some embodiments, the latter portion may comprise any type of information in any configuration (for example but not limited to graphical and/or textual) that is based at least in part on the classification of the anatomical structure. In some embodiments, the information comprises one or more types of information disclosed herein. In at least some embodiments, the information assists in performance of a medical procedure (other than collection of ultrasound image(s)).

In at least some embodiments, the composite image may have any form and may be generated in any manner. In some embodiments, the composite image may have the form of a single consolidated image, e.g., generated by overlaying the portion that is based at least in part on the classification of the anatomical structure on the portion that is the ultrasound image, which can be supplied to a display as a single image. In some other embodiments, the composite image may not have the form of a single consolidated image until displayed, e.g., generated as separate components that remain separate until displayed.

As stated above, in at least some embodiments, the ability to classify anatomical structures and generate a composite image (e.g., as disclosed herein) for display by a handheld imager (e.g., handheld imager 1300) facilitates a more portable solution for guidance to and/or location of anatomical features which can be operated without extensive training in ultrasonography. In at least some embodiments, such a handheld imager may be simpler to operate than generally available ultrasound imaging equipment. For example, in at least some embodiments, it enables more accurate puncture or probe insertion procedures by providing information to a person viewing the display about a depth and/or location of bone (and/or other structure(s)) with respect to the probe. In at least some embodiments, a handheld imager that displays the composite image is less expensive than generally available B-mode imaging equipment. Also, in at least some embodiments, the composite image disclosed herein provides an intuitive or easy-to-understand indication of a bone location or depth (or other structures and/or details in regard thereto) on a handheld imager, as compared to merely a B-mode sonogram on the handheld imager that can be difficult to interpret. In at least some embodiments, it can also reduce medical costs because the hand-held apparatus can be used for guided probe insertion or anatomical location thereby reducing likelihood of failure or complication during a probe insertion or other medical procedure. It is noted that the foregoing is explained in one or more exemplary embodiments in the transverse orientation. However, scanning the spine in longitudinal and oblique orientations is well within the scope of the present invention. Matched filters would be changed to detect the desired and anticipated shadow in each orientation.

The inventors of the present disclosure recognize that the described techniques can be used in other applications involving boney anatomy, lung or trachea. For example, the present invention can be used to distinguish placement of an intubation tube in the trachea or esophagus. Other examples that can employ the present system and method include: detection of rib shadowing when imaging the lungs, e.g., for detection of thoracentesis; detection of iliac crest for bone marrow biopsy; detection of facet joint for regional anesthesia; detection of the clavicle bone for regional anesthesia; or detection of the sacro-iliac joint for regional anesthesia.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments may be implemented in any of numerous ways. One or more aspects and embodiments of the present application involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various ones of the aspects described above. In some embodiments, computer readable media may be non-transitory media.

Additionally, it should be appreciated that according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smart phone or any other suitable portable or fixed electronic device.

Figure 15:
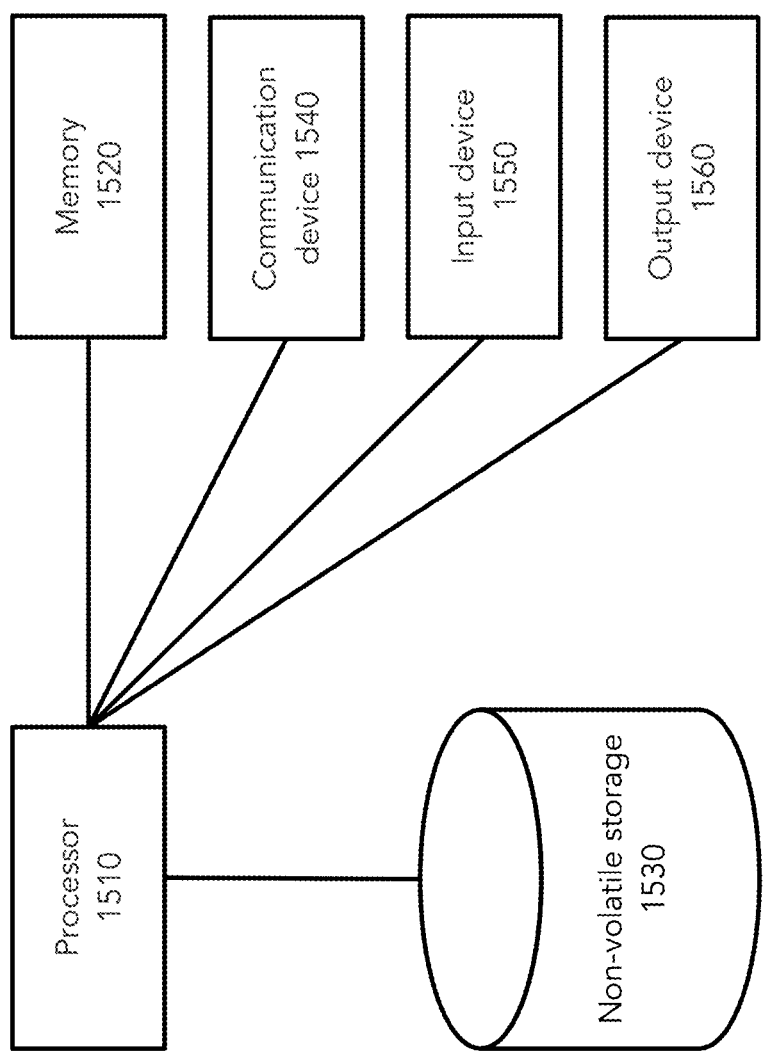
FIG. 15 is a schematic block diagram of a computer architecture, in accordance with some embodiments.

FIG. 15 is a block diagram of a computer architecture 1500 according to some embodiments. In some embodiments, one or more of the systems (or portion(s) thereof), apparatus (or portion(s) thereof) and/or devices (or portion(s) thereof) disclosed herein may have an architecture that is the same as and/or similar to one or more portions of the architecture 1500.

In some embodiments, one or more of the methods (or portion(s) thereof) disclosed herein may be performed by a system, apparatus and/or device having an architecture that is the same as or similar to the architecture 1500 (or portion(s) thereof). The architecture may be implemented as a distributed architecture or a non-distributed architecture.

Referring to FIG. 15, in accordance with at least some embodiments, the architecture 1500 may include one or more processors 1510 and one or more articles of manufacture that comprise non-transitory computer-readable storage media (e.g., memory 1520 and one or more non-volatile storage media 1530). The processor 1510 may control writing data to and reading data from the memory 1520 and the non-volatile storage device 1530 in any suitable manner, as the aspects of the disclosure provided herein are not limited in this respect. The storage media may store one or more programs and/or other information for operation of the architecture 1500. In at least some embodiments, the one or more programs include one or more instructions to be executed by the processor 1510 to provide one or more portions of one or more tasks and/or one or more portions of one or more methods disclosed herein. In some embodiments, other information includes data for one or more portions of one or more tasks and/or one or more portions of one or more methods disclosed herein. To perform any of the functionality described herein, the processor 1510 may execute one or more processor-executable instructions stored in one or more non-transitory computer-readable storage media (e.g., the memory 1520), which may serve as non-transitory computer-readable storage media storing processor-executable instructions for execution by the processor 1510.

The terms "program" or "software" are used herein in a generic sense to refer to any type of computer code or set of computer-executable instructions that may be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more communication devices 1540, which may be used to interconnect the computer to one or more other devices and/or systems, such as, for example, one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, a computer may have one or more input devices 1550 and/or one or more output devices 1560. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

It should be understood that the features disclosed herein can be used in any combination or configuration. Thus, for example, in some embodiments, any one or more of the features disclosed herein may be used without any one or more other feature disclosed herein.

Unless stated otherwise, a computing device is any type of device that includes at least one processor.

Unless stated otherwise, a processing device is any type of device that includes at least one processor.

Unless stated otherwise, a processing system is any type of system that includes at least one processor.

Unless stated otherwise, a mobile (or portable) computing device includes, but is not limited to, any computing device that may be carried in one or two hands and/or worn.

Unless stated otherwise, a processor may comprise any type of processor. For example, a processor may be programmable or non-programmable, general purpose or special purpose, dedicated or non-dedicated, distributed or non-distributed, shared or not shared, and/or any combination thereof. A processor may include, but is not limited to, hardware, software (e.g., low-level language code, high-level language code, microcode), firmware, and/or any combination thereof.

Unless stated otherwise, a program may include, but is not limited to, instructions in a high-level language, low-level language, machine language and/or other type of language or combination thereof.

Unless stated otherwise, a "communication link" may comprise any type(s) of communication link(s), for example, but not limited to, wired links (e.g., conductors, fiber optic cables) or wireless links (e.g., acoustic links, radio links, microwave links, satellite links, infrared links or other electromagnetic links) or any combination thereof, each of which may be public and/or private, dedicated and/or shared. In some embodiments, a communication link may employ a protocol or combination of protocols including, for example, but not limited to the Internet Protocol.

Unless stated otherwise, information may include data and/or any other type of information.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. A method, comprising:
   obtaining, by a processor, ultrasound data generated based on one or more ultrasound signals from an imaged region of a subject;
   determining, by the processor, a shadow profile based on:
   (1) creating a shadow intensity image from the ultrasound data by calculating a weighted integrated sum of ultrasound data of a plurality of depth samples having values greater in depth than a current depth sample plus an offset, wherein the offset is greater than zero, and wherein the plurality of depth samples used to calculate the weighted integrated sum change depending on a depth or depths of the ultrasound data of the plurality of depth samples; and
   (2) determining from each A-line of a plurality of A-lines of the shadow intensity image a depth corresponding to a location of a boundary between a shadow region and tissue;
   convolving, by the processor, the shadow profile with a matched shadow profile filter approximating a location or locations of one or more known anatomical landmarks, thereby creating a filtered shadow profile;
   identifying, by the processor, an anatomical landmark present in the filtered shadow profile by using at least one of a most prominent peak or a subpeak of the most prominent peak located in the shadow profile;
   classifying, by the processor, the anatomical landmark using the at least one or more of the most prominent peak or the subpeak of the most prominent peak located in the shadow profile;
   displaying, on a display of a handheld ultrasound imager, a composite image based on the ultrasound data and based on the identified and classified anatomical landmark; and
   performing a probe insertion procedure based on the displayed composite image.

2. The method of claim 1, wherein said identifying the anatomical landmark present in the imaged region comprises:
   receiving information indicative of a target anatomy;
   determining an anticipated shadow based on the information indicative of the target anatomy; and identifying, based on the shadow profile and the anticipated shadow, the anatomical landmark present in the imaged region.

3. The method of claim 1, wherein said identifying the anatomical landmark present in the imaged region comprises:
identifying a feature in the shadow profile; and
classifying the feature in the shadow profile as a specific anatomical landmark, for example, a midline.

4. The method of claim 3, wherein the specific anatomical landmark is a midline.

5. The method of claim 3, further comprising:
identifying a second feature in the shadow profile; and
comparing the feature and the second feature in the shadow profile.

6. The method of claim 5, wherein the comparing the feature in the shadow profile and the second feature in the shadow profile comprises:
determining a metric for the feature in the shadow profile;
determining a metric for the second feature in the shadow profile; and
comparing the metric for the feature in the shadow profile and the metric for the second feature in the shadow profile.

7. The method of claim 6, wherein the comparing the metric for the feature in the shadow profile and the metric for the second feature in the shadow profile comprises:
determining a difference of the metric for the feature in the shadow profile and the metric for the second feature in the shadow profile.

8. The method of claim 6, wherein the comparing the metric for the feature in the shadow profile and the metric for the second feature in the shadow profile comprises:
determining a ratio of the metric for the feature in the shadow profile and the metric for the second feature in the shadow profile.

9. The method of claim 1, wherein the one or more ultrasound signals comprise at least one of the plurality of A-lines, a received echo signal, a radiofrequency signal, a digitized radiofrequency signal, a pulse echo signal, an acoustic reflection line, and a transmit receive line.

10. A system for displaying a composite ultrasound image to guide insertion of a probe into a subject's cavity, the system comprising:
a handheld ultrasound imager;
a probe;
at least one computer hardware processor configured to perform:
obtaining ultrasound data generated based on one or more ultrasound signals from an imaged region of a subject;
determining a shadow profile based on:
(1) creating a shadow intensity image from the ultrasound data by calculating a weighted integrated sum of ultrasound data of a plurality of depth samples having values greater in depth than a current depth sample plus an offset, wherein the offset is greater than zero, and wherein the plurality of depth samples used to calculate the weighted integrated sum change depending on a depth or depths of the ultrasound data of the plurality of depth samples; and
(2) determining from each A-line of a plurality of A-lines of the shadow intensity image a depth corresponding to a location of a boundary between a shadow region and tissue;
convolving the shadow profile with a matched shadow profile filter approximating a location or locations of one or more known anatomical landmarks, thereby creating a filtered shadow profile;
identifying an anatomical landmark present in the filtered shadow profile by using at least one of a most prominent peak or a subpeak of the most prominent peak located in the shadow profile;
classifying the anatomical landmark using the at least one or more of the most prominent peak or the subpeak of the most prominent peak located in the shadow profile;
using the handheld ultrasound imager to display a composite ultrasound image based on the ultrasound data and based on the identification and classification of the anatomical landmark; and
using the displayed composite ultrasound image to guide insertion of the probe into the subject's cavity.

11. The system of claim 10, wherein said identifying the anatomical landmark present in the imaged region comprises:
filtering the shadow profile; and
identifying, based on the filtered shadow profile, the anatomical landmark present in the imaged region.

12. The system of claim 10, wherein said determining the shadow profile based on the ultrasound data comprises:
determining shadow intensity data based on the ultrasound data; and
determining the shadow profile based on non-linear processing of the shadow intensity data.

13. The system of claim 10, wherein said identifying the anatomical landmark present in the imaged region comprises:
receiving information indicative of a target anatomy;
determining an anticipated shadow based on the information indicative of the target anatomy;
determining a measure of similarity between the shadow profile and the anticipated shadow; and
identifying, based on the measure of similarity between the shadow profile and the anticipated shadow, the anatomical landmark present in the imaged region.

14. The system of claim 10, wherein said identifying the anatomical landmark present in the imaged region comprises:
receiving information indicative of a target anatomy;
determining an anticipated shadow based on the information indicative of the target anatomy; and
identifying, based on the shadow profile and the anticipated shadow, the anatomical landmark present in the imaged region.

15. The system of claim 10, wherein said identifying the anatomical landmark present in the imaged region comprises:
identifying a feature in the shadow profile; and
classifying the feature in the shadow profile as the anatomical landmark.

16. The system of claim 10, wherein the one or more ultrasound signals comprise at least one of the plurality of A-lines, a received echo signal, a radiofrequency signal, a digitized radiofrequency signal, a pulse echo signal, an acoustic reflection line, and a transmit receive line.

* * * * *